(12) United States Patent
Beaty et al.

(10) Patent No.: US 7,570,798 B2
(45) Date of Patent: *Aug. 4, 2009

(54) METHOD OF MANUFACTURING BALL ARRAY DEVICES USING AN INSPECTION APPARATUS HAVING ONE OR MORE CAMERAS AND BALL ARRAY DEVICES PRODUCED ACCORDING TO THE METHOD

(76) Inventors: Elwin M. Beaty, 4665 S. Ash Ave., Suite G20, Tempe, AZ (US) 85282; David P. Mork, 4665 S. Ash Ave., Suite G20, Tempe, AZ (US) 85282

( * ) Notice: Subject to any disclaimer, the term of this patent is extended or adjusted under 35 U.S.C. 154(b) by 0 days.

This patent is subject to a terminal disclaimer.

(21) Appl. No.: 11/735,978

(22) Filed: Apr. 16, 2007

(65) Prior Publication Data

US 2007/0183645 A1 Aug. 9, 2007

Related U.S. Application Data

(63) Continuation-in-part of application No. 11/069,758, filed on Feb. 28, 2005, which is a continuation of application No. 09/351,892, filed on Jul. 13, 1999, now Pat. No. 6,862,365, which is a continuation-in-part of application No. 09/008,243, filed on Jan. 16, 1998, now Pat. No. 6,072,898.

(51) Int. Cl.
*G06K 9/00* (2006.01)
(52) U.S. Cl. ............... 382/145; 382/146; 348/126; 250/559.34

(58) Field of Classification Search ............. 250/200, 250/559.01, 559.19, 559.22, 559.23, 559.29, 250/559.31, 559.34, 559.36, 559.44; 356/237.1, 356/237.2, 237.3, 237.4; 382/141, 144, 145, 382/146, 149, 150, 151, 153, 154; 702/127, 702/150, 152, 153; 348/61, 86, 87, 94, 95, 348/135, 126; 700/90, 245, 258, 259
See application file for complete search history.

(56) References Cited

U.S. PATENT DOCUMENTS

2007/0183646 A1* 8/2007 Beaty et al. ............. 382/145

OTHER PUBLICATIONS

Final Decision, *Scanner Technologies Corporation v. ICOS Vision Systems Corporation N.V.*, Civil Action Nos. 2007-1399 and 2008-1081, United States Court of Appeals for the Federal Circuit—Jun. 19, 2008.

(Continued)

*Primary Examiner*—Sheela C Chawan
(74) *Attorney, Agent, or Firm*—The Marbury Law Group, PLLC

(57) ABSTRACT

An apparatus for three dimensional inspection of an electronic part which has a camera and illuminator for imaging a first view of the electronic part. An optical element is positioned to reflect a different view of the electronic part into the camera, and the camera thus provides an image of the electronic part having differing views of the electronic part. An image processor applies calculations on the differing views to calculate a three dimensional position of at least one portion of the electronic part.

36 Claims, 30 Drawing Sheets

OTHER PUBLICATIONS

Opinion, *Scanner Technologies Corp. v. ICOS Vision Systems, N.V.*, No. 1:00-cv-04992-DC (S.D.N.Y. 2007), appeal docketed, No. 2007-1399 (Fed. Cir. Jun. 22, 2007).

Final Judgment, *Scanner Technologies Corp. v. ICOS Vision Systems, N.V.*, No. 1:00-cv-04992-DC (S.D.N.Y. 2007), appeal docketed, No. 2007-1399 (Fed. Cir. Jun. 22, 2007).

Notice of Appeal, *Scanner Technologies Corp. v. ICOS Vision Systems, N.V.*, No. 00-Civ.-4992, (S.D.N.Y. 2007), appeal docketed, No. 2007-1399 (Fed. Cir. Jun. 22, 2007).

Docketing Statement, *Scanner Technologies Corp. v. ICOS Vision Systems, N.V.*, No. 1:00-cv-04992-DC (S.D.N.Y. 2007), appeal docketed, No. 2007-1399 (Fed. Cir. Jun. 22, 2007).

\* cited by examiner

2 SIDE VIEWS
CALIBRATION PATTERN

2 SIDE VIEWS
BALLS

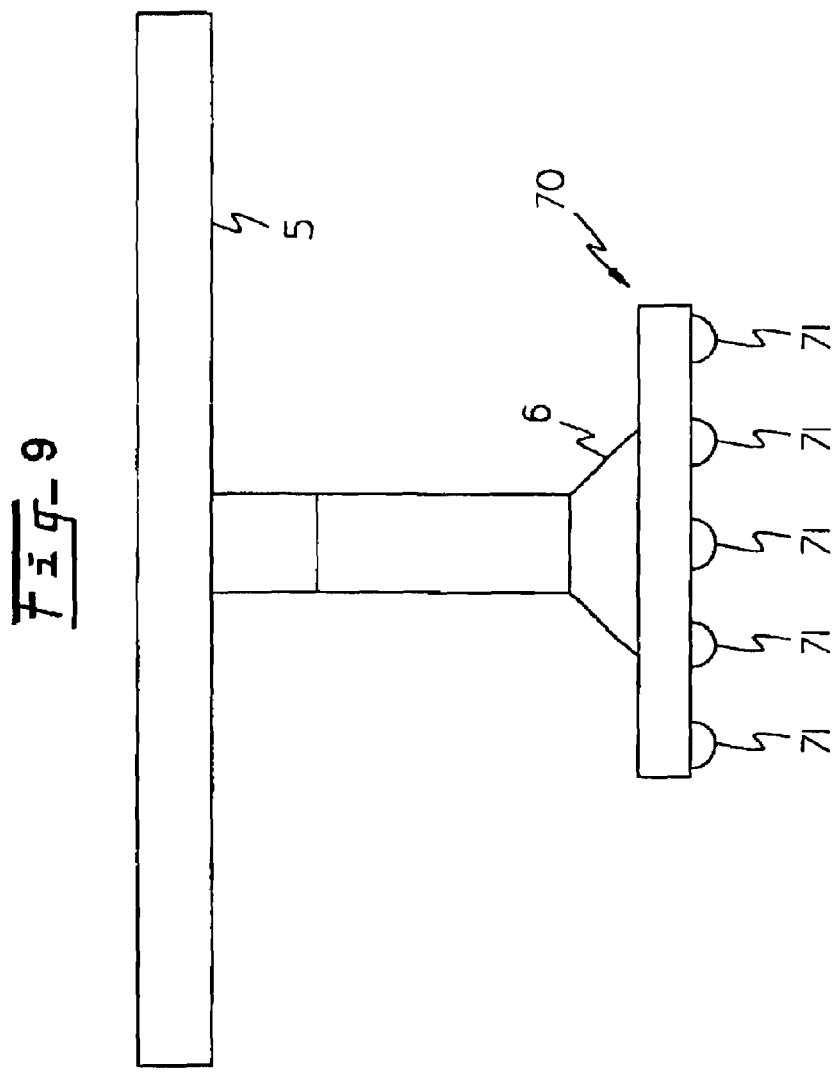

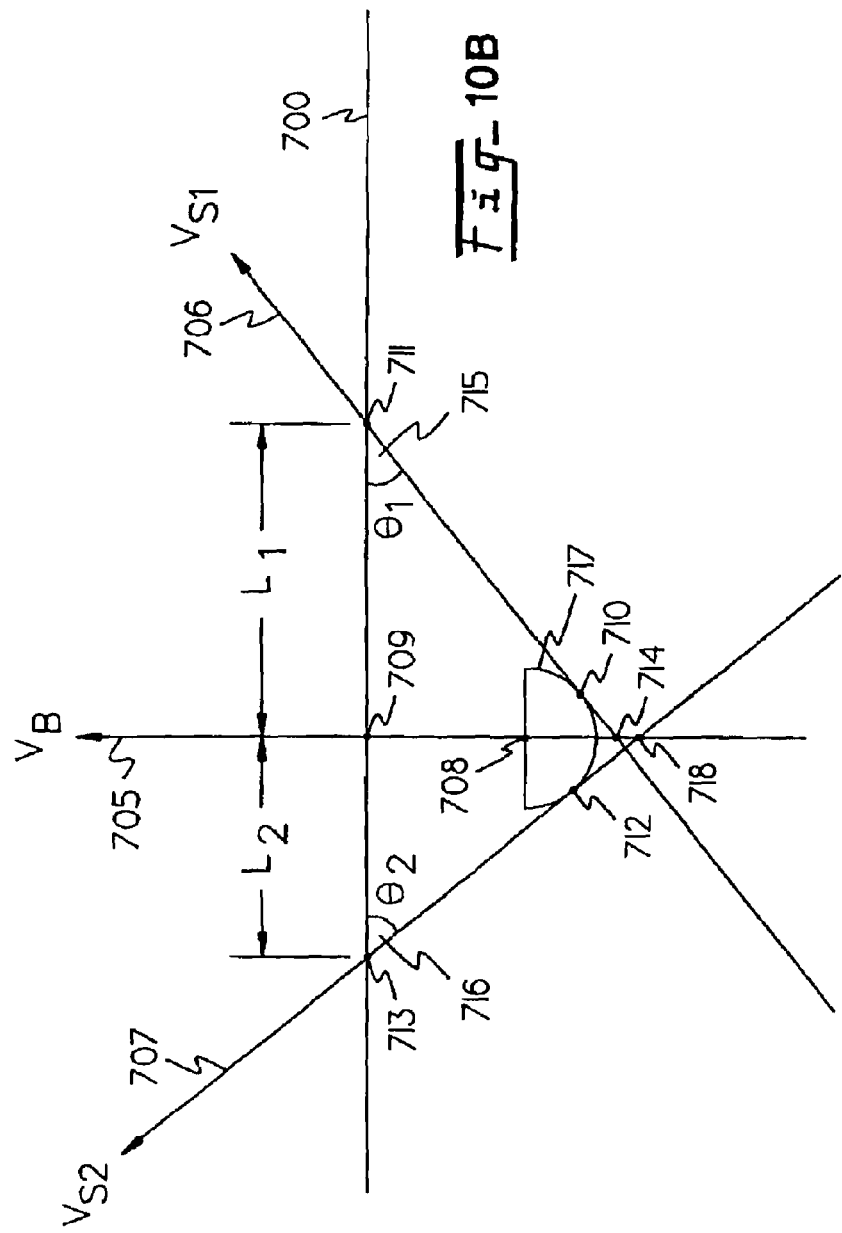

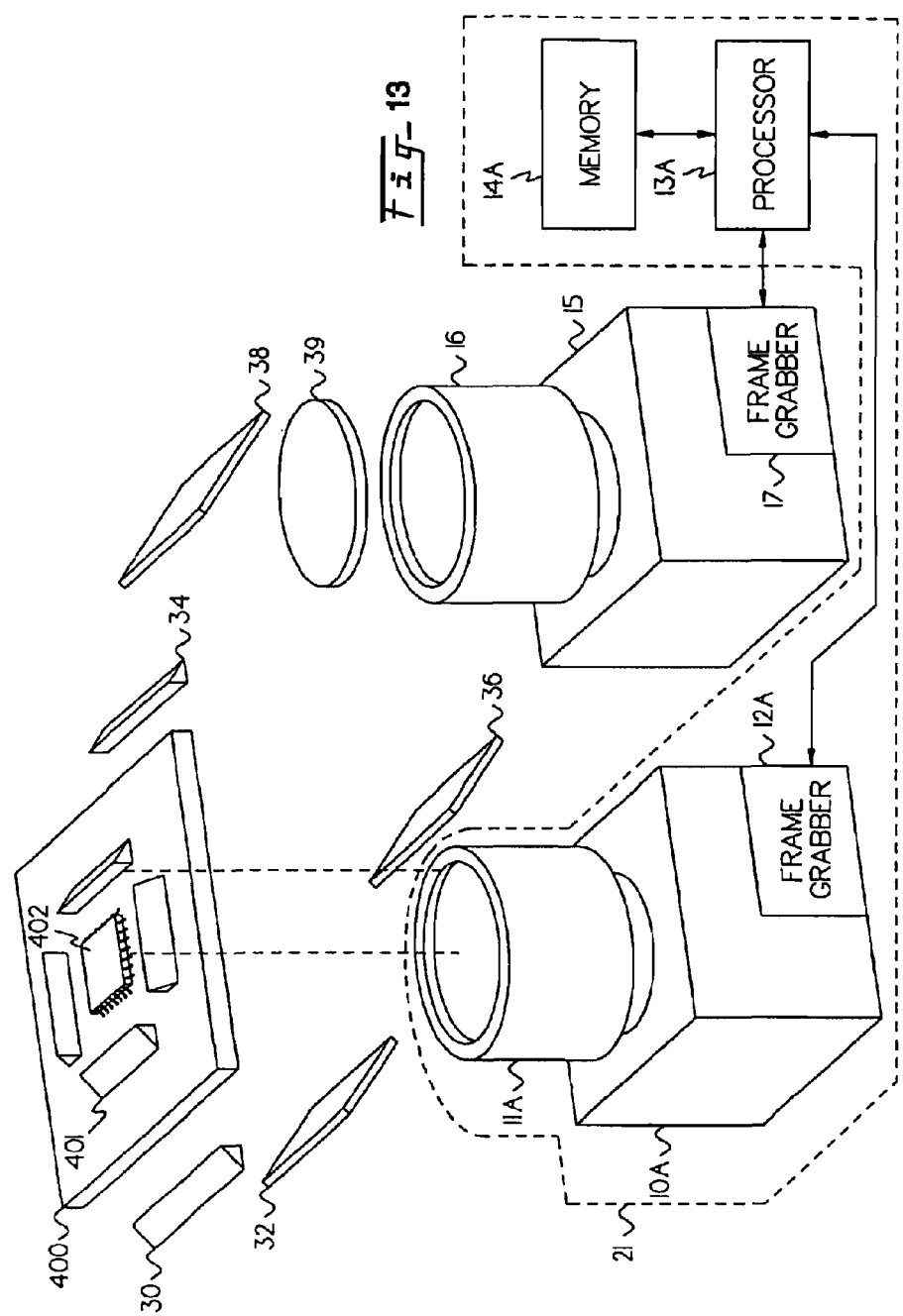

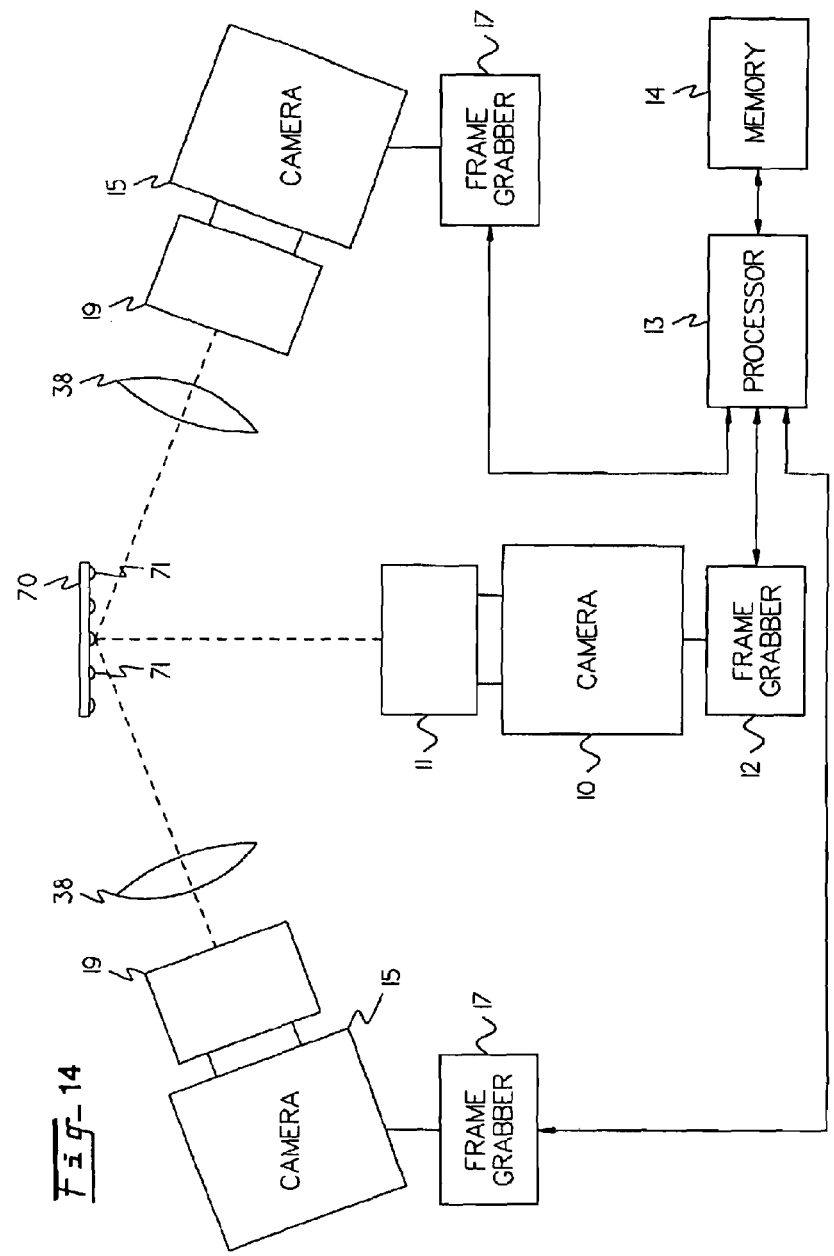

CALIBRATION RETICLE

IMAGE

BGA

IMAGE

METHOD OF MANUFACTURING BALL ARRAY DEVICES USING AN INSPECTION APPARATUS HAVING ONE OR MORE CAMERAS AND BALL ARRAY DEVICES PRODUCED ACCORDING TO THE METHOD

CROSS REFERENCE TO RELATED APPLICATIONS

This application is a continuation-in-part of pending application Ser. No. 11/069,758, filed Feb. 28, 2005, which is a continuation of application Ser. No. 09/351,892, filed Jul. 13, 1999, now U.S. Pat. No. 6,862,365, which is a continuation-in-part of application Ser. No. 09/008,243, filed Jan. 16, 1998, now U.S. Pat. No. 6,072,898. The application Ser. No. 11/069,758 and U.S. Pat. Nos. 6,862,365 and 6,072,898 are incorporated by reference herein, in their entireties, for all purposes.

NOTICE REGARDING COPYRIGHT

A portion of the disclosure of this patent document contains material that is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

This invention relates to three dimensional inspection of leads of ball array devices. More particularly, the invention relates to a method for three dimensional inspection and ball array devices manufactured using the three dimensional inspection method.

BACKGROUND INFORMATION

Prior art three dimensional inspection systems have involved laser range finding technology, moire interferometry, structured light patterns or two cameras. The laser range finding method directs a focused laser beam onto the Ball Grid Array, BGA, and detects the reflected beam with a sensor. Elements of the BGA are determined in the X, Y and Z dimensions utilizing a triangulation method. This method requires a large number of measurement samples to determine the dimensions of the BGA resulting in longer inspection times. This method also suffers from specular reflections from the smooth surfaces of the solder balls resulting in erroneous data.

Moire interferometry utilizes the interference of light waves generated by a diffraction grating to produce a pattern of dark contours on the surface of the BGA. These contours are of known distance in the Z dimension from the diffraction grating. By counting the number of contours from one point on the BGA to another point on the BGA, the distance in the Z dimension between the two points can be determined. This method suffers from the problem of low contrast contour lines resulting in missed counting of the number of contours and resulting in erroneous data. This method also suffers from the contour lines merging at surfaces with steep slopes, such as the sides of the balls on the BGA, resulting in an incorrect count of the number of contours and resulting in erroneous data.

Structured light systems project precise bands of light onto the part to be inspected. The deviation of the light band from a straight line is proportional to the distance from a reference surface. The light bands are moved across the part, or alternately the part is moved with respect to the light bands, and successive images are acquired. The maximum deviation of the light band indicates the maximum height of a ball. This method suffers from specular reflections due to the highly focused nature of the light bands resulting in erroneous data. This method further suffers from increased inspection times due to the number of images required.

Two camera systems utilize one camera to view the BGA device in the normal direction to determine X and Y dimensions and the second camera to view the far edges of the balls from an angle. The two images are combined to determine the apparent height of each ball in the Z dimension utilizing a triangulation method. This method suffers from the need for a higher angle of view of the ball from the second camera resulting in looking at a point significantly below the top of the ball for BGA's having fine pitch. This method also suffers from limited depth of focus for the second camera limiting the size of BGA's that can be inspected. This system can only inspect BGA's and not other device types such as gullwing and J lead devices.

The prior art does not provide two separate and opposite side views permitting larger BGA's to be inspected or non-linear optics to enhance the separation between adjacent ball images in the side perspective view.

It is therefore a motivation of the invention to improve the accuracy of the measurements, the speed of the measurements, the ability to measure all sizes and pitches of BGA's and to measure other devices including gullwing and J lead parts in a single system.

SUMMARY OF THE INVENTION

The invention provides an apparatus for three dimensional inspection of an electronic part, wherein the apparatus is calibrated using a precision pattern mask with dot patterns deposited on a calibration transparent reticle, the apparatus for three dimensional inspection of an electronic part comprising a camera and an illuminator for imaging the electronic part, the camera being positioned to obtain a first view of the electronic part, a means for light reflection positioned to reflect a different view of the electronic part into the camera, wherein the camera provides an image of the electronic part having differing views of the electronic part, and a means for image processing the image of the electronic part that applies calculations on the differing views of the image to calculate a three dimensional position of at least one portion of the electronic part.

The invention further comprises a ring light. The means for light reflection could further comprise a mirror, a prism, or a curved mirror. The electronic part may be a ball grid array, balls on a wafer, or balls on a die.

The means for imaging provides the image to a frame grabber board. The frame grabber board provides an image data output to a processor to perform a three dimensional inspection of the part.

The apparatus may further comprise a nonlinear optical element to magnify the second image in one dimension. In the apparatus a maximum depth of focus of a side perspective view allows for a fixed focus system to inspect larger electronic parts, with one perspective view imaging one portion of the electronic part and a second perspective view imaging a second portion of the electronic part. Also, in the apparatus a maximum depth of focus of a side perspective view includes an area of the electronic part including a center row of balls. Furthermore, all of the balls on the electronic part may be in focus resulting in two perspective views for each ball.

The invention comprises a means for inspecting gullwing and J lead devices.

According to one embodiment, a method is practiced for manufacturing a ball array device having plural leads. The method includes providing a fixed optical imaging system with at least one camera, and calibrating the fixed optical imaging system with a planar precision pattern disposed in a fixed position. The method further includes, and obtaining a single bottom view image, as well as a single side view image, of the leads using the calibrated system, and calculating an inspection result by combining information from the single bottom view image and the single side view image. The ball array device is selected as a manufactured product using the calculated inspection result.

According to another embodiment, a method is practiced for manufacturing a ball array device having plural leads. The method includes providing a fixed optical imaging system with at least one camera, and calibrating the fixed optical imaging system with a planar precision pattern disposed in a fixed focus position. The method further includes obtaining, using the calibrated system, a bottom view image with donut shaped reflections from the leads and a side view image with crescent shaped reflections from the leads. The method further includes finding locations of the donut shaped reflections from the leads and locations of the crescent shaped reflections from the leads, and then calculating a Z value for each lead by combining information from the locations of the donut shaped reflections and the locations of the crescent shaped reflections. A coplanarity value for the ball array device is calculated by using the Z value for each lead, and an inspection result is determined by comparing the coplanarity value to a predetermined tolerance value. The ball array device is selected as a manufactured product based upon the inspection result.

According to yet another embodiment, a method is practiced for manufacturing a ball array device having plural leads. The method includes providing an imaging system with at least one camera, at least one lens, at least one illumination source, at least one processor and memory. The method further includes obtaining a single bottom view image, as well as a single side view image, of the leads using the imaging system. The method also includes finding a subpixel location of each lead in the single bottom view image, and finding a subpixel location of each lead in the single side view image. A Z value is calculated for each lead by combining information from the subpixel location of the lead in the single bottom view image and the subpixel location of the same lead in the single side view image, and a coplanarity value is calculated for the ball array device by using information from the Z value of each lead and parameters determined during a calibration. An inspection result is determined by comparing the coplanarity value to a predetermined tolerance value, and the ball array device is selected based upon the inspection result.

According to a further embodiment, a method is practiced for manufacturing a ball array device having plural leads. The method includes providing a fixed optical imaging system with at least one camera, at least one lens, at least one illumination source, at least one processor and memory. The imaging system is calibrated with a planar precision pattern disposed in a fixed focus position. The method further includes obtaining a single bottom view image of the leads using the calibrated imaging system, and obtaining a single side view image of the leads using the calibrated imaging system. A subpixel location of a reflection from each lead is found in the single bottom view image, and a subpixel location of a reflection from each lead is found in the single side view image. A Z value is calculated for each lead by combining information from the subpixel location of a reflection from the lead in the single bottom view image and the subpixel location of the reflection from the same lead in the single side view image, and a coplanarity value is calculated for the ball array device by using information from the Z value of each lead. An inspection result is determined by comparing the coplanarity value to a predetermined tolerance value, and the ball array device is selected based upon the inspection result.

According to another embodiment, a method is practiced for manufacturing a ball array device having plural leads. The method includes providing an imaging system with at least one camera, and calibrating the imaging system with a planar precision pattern disposed in a fixed focus position. The method further includes obtaining two differing views of the leads in at least one image using the calibrated imaging system, obtaining a donut shaped reflection from each lead and a crescent shaped reflection from each lead in the at least one image, and finding at least two reference positions of each lead in the at least one image. A Z value of each lead is calculated using the at least two reference positions of each lead, and a coplanarity value is calculated using information from the Z value of each lead. An inspection result is determined by comparing the coplanarity value to a tolerance value, and the ball array device is selected as a manufactured product depending upon the inspection result.

According to another embodiment, ball array devices are provided, manufactured according to any of the methods summarized above.

According to yet another embodiment, an electronic product is provided by including a ball array device manufactured as summarized above. The electronic product may be, for example, an automotive controller, a personal computer, a digital camera, a graphics board, a memory device, a motherboard, a music player, a networking device, a telephone, a cell phone, a television, a video game console and a video player.

The lead may be a curved surface lead, a ball, a ball grid array, a formed wire, a stamped metal form, a column, a contact, a pad, a pins, a towers, a post, a micro-pin, and a pedestal or similar object that can be imaged from two separate directions.

The processor processes the pixel values to find a rotation, an X placement value and a Y placement value of the part relative to world X and Y coordinates by finding points on four sides of the part.

The invention further provides for using a part definition file that contains measurement values for an ideal part, calculating an expected position for each lead of the part for a bottom view using the measurement values from the part definition file and the X placement value and Y placement value.

The invention further provides for using a search procedure on the image data to locate the lead.

The invention further provides for determining a lead center location and a lead diameter in pixels and storing the lead center location and lead diameter in memory.

The invention further provides for calculating an expected position of a center of each lead in both side perspective views in the image using a known position of each side view from calibration.

The invention further provides for using a subpixel edge detection method to locate a reference point on each lead.

The invention further provides for converting the pixel values into world locations by using pixel values and parameters determined during calibration wherein the world locations represent physical locations of the lead with respect to world coordinates defined during calibration.

The invention further provides for the calculation of a Z height of each lead in world coordinates in pixel values by combining a location of a center of a lead from a bottom view with a reference point of the same lead from a side perspective view.

The invention further provides for converting the world values to part values using the rotation, the X placement value and the Y placement value to define part coordinates for the ideal part where the part values represent physical dimensions of the lead including lead diameter, lead center location in X part and Y part coordinates and lead height in Z world coordinates.

The invention further provides for comparing ideal values defined in the part file to calculate deviation values that represent a deviation of the center of the lead from its ideal location. The deviation values may include lead diameter in several orientations with respect to the X placement value and Y placement value, lead center in the X direction, Y direction and radial direction, lead pitch in the X direction and Y direction and missing and deformed leads, further comprising the step of calculating the Z dimension of the lead with respect to the seating plane based on the Z world data.

The invention further provides for comparing the deviation values to predetermined tolerance values with respect to an ideal part as defined in the part definition file to provide a lead inspection result.

BRIEF DESCRIPTION OF THE DRAWINGS

To illustrate this invention, preferred embodiments will be described herein with reference to the accompanying drawings.

FIG. 9 shows an apparatus for presenting a BGA for inspection.

FIGS. 10A and 10B show an example ball of a ball grid array with associated geometry as used with a method of the invention for determining the Z position of a ball using two side perspective views.

FIG. 13 shows the apparatus of the invention for the three dimensional inspection of ball grid array devices, gullwing devices and J lead devices.

FIG. 14 shows the apparatus of the invention for the three dimensional inspection of parts utilizing three cameras.

DETAILED DESCRIPTION

In one embodiment of the invention, the method and apparatus disclosed herein is a method and apparatus for calibrating the system by placing a pattern of calibration dots of known spacing and size on the bottom plane of a calibration reticle. From the precision dots the missing state values of the system are determined allowing for three dimensional inspection of balls on ball grid array devices, BGA devices or balls on wafers or balls on die. In one embodiment of the invention the system may also inspect gullwing and J lead devices as well as ball grid arrays.

Figure 1A:
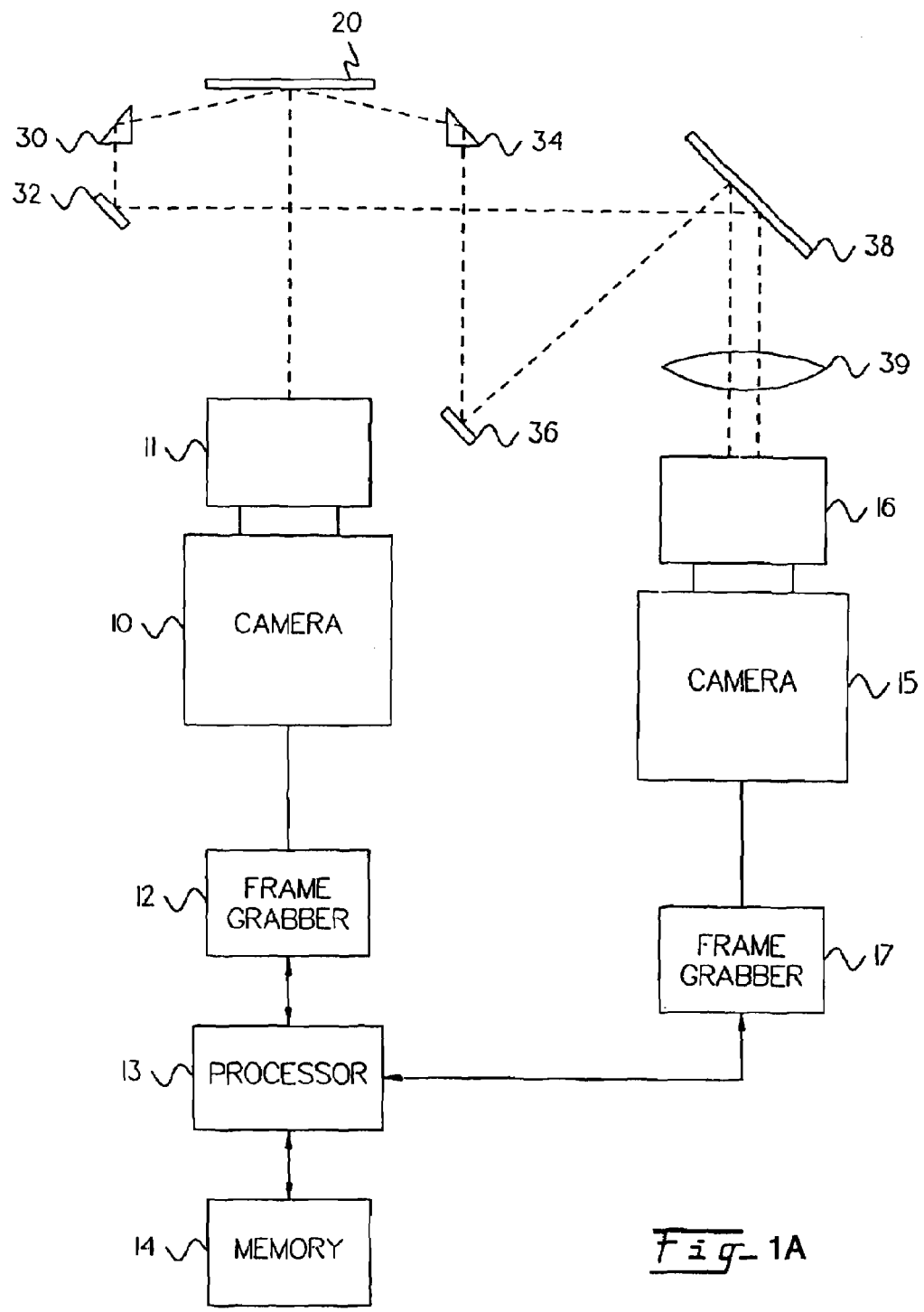
FIG. 1A shows the apparatus of the invention for system calibration.
Figure 8A:
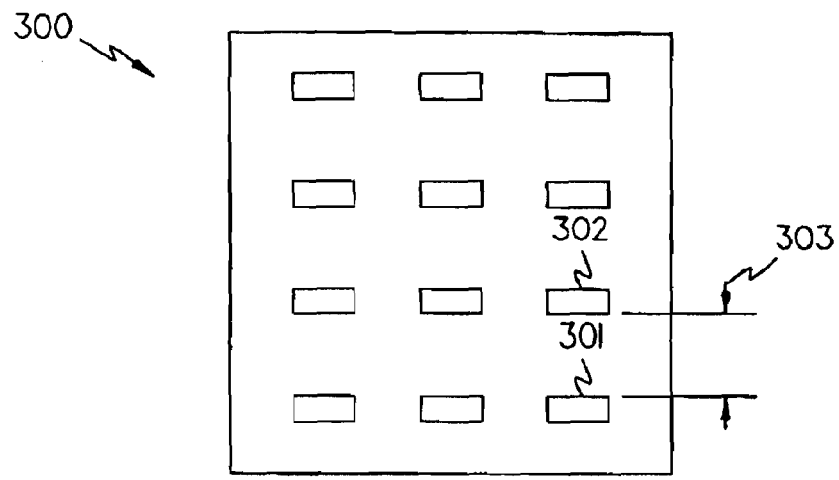
FIG. 8A shows a side perspective image of the calibration pattern magnified in one dimension.

Refer now to FIG. 1A which shows the apparatus of the invention configured with a calibration reticle for use during calibration of the state values of the system. The apparatus obtains what is known as a bottom image 50 of the calibration reticle 20. To take the bottom image 50 the apparatus includes a camera 10 with a lens 11 and calibration reticle 20 with a calibration pattern 22 on the bottom surface. The calibration pattern 22 on the reticle 20 comprises precision dots 24. The camera 10 is located below the central part of the calibration reticle 20 to receive an image 50 described in conjunction with FIG. 1B. In one embodiment the camera 10 comprises an image sensor. The image sensor may be a charged coupled device array. The camera 10 is connected to a frame grabber board 12 to receive the image 50. The frame grabber board 12 provides an image data output to a processor 13 to perform a two dimensional calibration as described in conjunction with FIG. 2A. The processor 13 may store an image in memory 14. The apparatus of the invention obtains an image of a pair of side perspective views and includes using a camera 15 with a lens 16 and a calibration reticle 20. The camera 15 is located to receive an image 60, comprising a pair of side perspective views, described in conjunction with FIG. 1B. Fixed optical elements 30, 32 and 38 provide a first side perspective view and fixed optical elements 34, 36, 38 for a second side perspective view. The fixed optical elements 30, 32, 34, 36 and 38 may be mirrors or prisms. As will be appreciated by those skilled in the art additional optical elements may be incorporated. The camera 15 is connected to a frame grabber board 17 to receive the image 60. The frame grabber board 17 provides an image data output to a processor 13 to perform a two dimensional inspection as described in conjunction with FIG. 2B. The processor 13 may store an image in memory 14. In one embodiment of the invention, the apparatus may contain a nonlinear optical element 39 to magnify the side perspective image 60 in one dimension as shown in FIG. 8A. In another embodiment of the invention optical element 38 may be a nonlinear element. The nonlinear optical elements 38 and 39 may be a curved mirror or a lens.

Figure 1B:
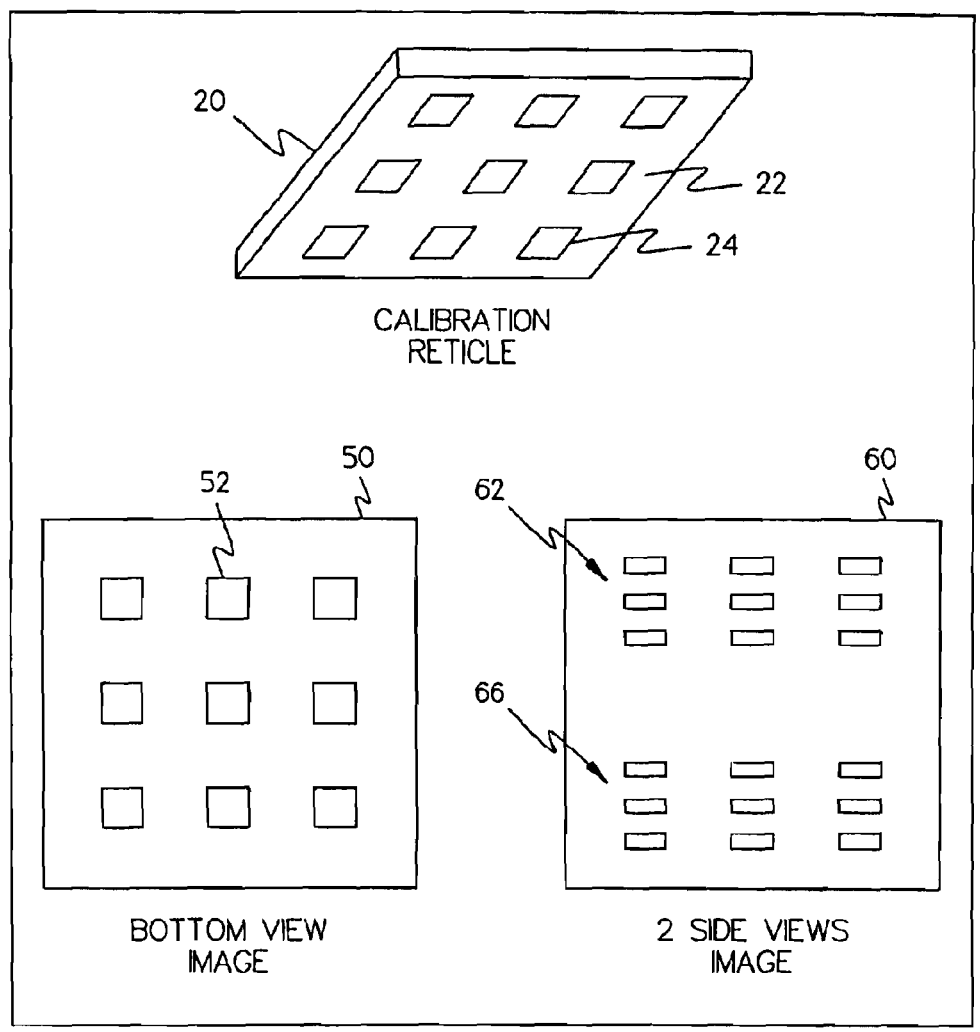
FIG. 1B shows an example calibration pattern and example images of the calibration pattern acquired by the system.

FIG. 1B show an example image 50 from camera 10 and an example image 60 from camera 15 acquired by the system. The image 50, a bottom view of dot pattern 22, shows dots 52 acquired by camera 10. The dot pattern contains precision dots 24 of known dimensions and spacing. The precision dots 24 are located on the bottom surface of the calibration reticle 20. The image 60 shows two side perspective views of the dot pattern 22. A first side perspective view in image 60 contains images 62 of dots 24 and is obtained by the reflection of the image of the calibration reticle dot pattern 22 off of fixed optical elements 30, 32 and 38 into camera 15. A second side perspective view in image 60 contains images 66 of dots 24 and is obtained by the reflection of the image of the calibration reticle dot pattern 22 off of fixed optical elements 34, 36 and 38 into camera 15.

Optical element 36 is positioned to adjust the optical path length of a second side perspective view to equal the optical path length of a first side perspective view. Those skilled in the art will realize that any number of perspective views can be utilized by the invention. In one embodiment of the invention, the maximum depth of focus of a side perspective view includes an area of the reticle including the center row of dots. This allows for a fixed focus system to inspect larger parts, with one perspective view imaging half of the part and the second perspective view imaging the other half of the part.

Figure 2A:
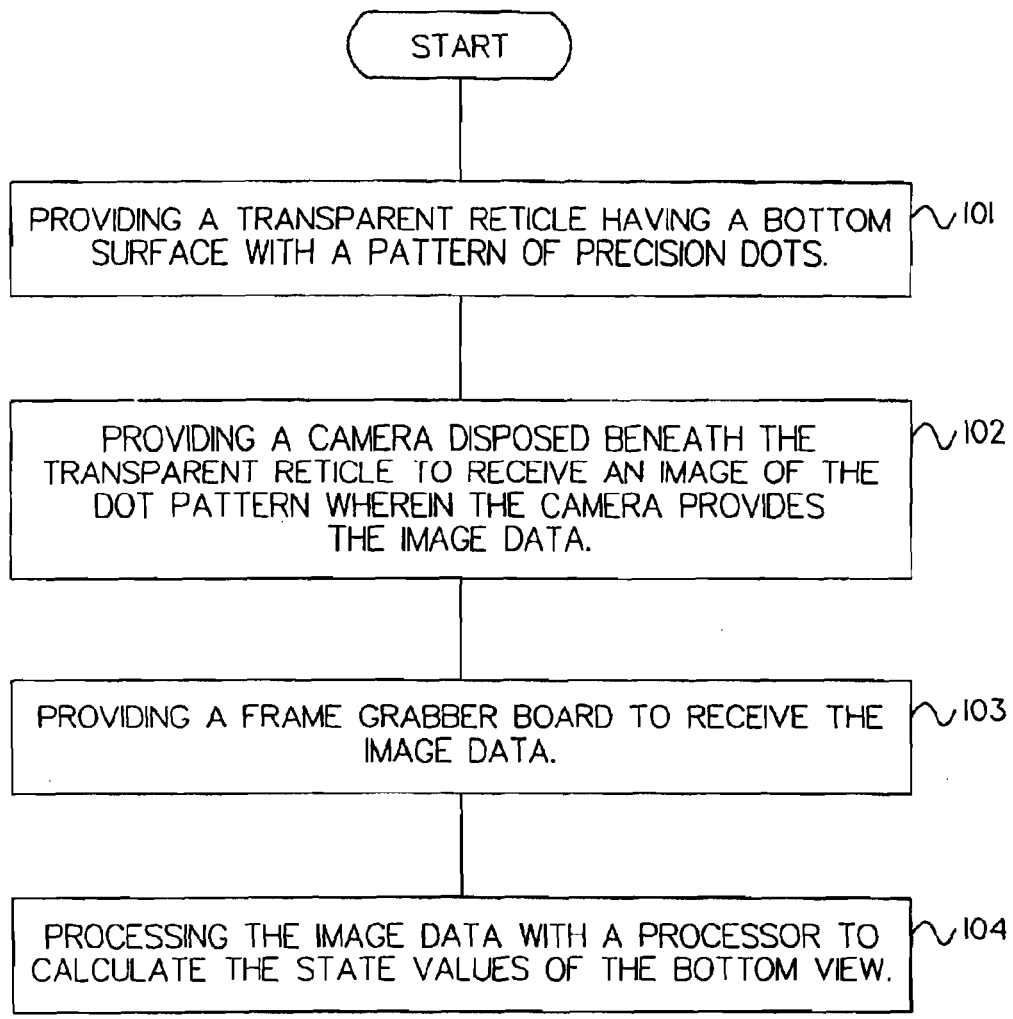
FIG. 2A shows a flow chart of a method of the invention used for calibration of the bottom view.

FIG. 2A shows a flow diagram for the calibration of the bottom view of the system. The method starts in step 101 by providing a transparent reticle 20 having a bottom surface containing a dot pattern 22, comprising precision dots 24 of known dimensions and spacing. The method in step 102 provides a camera 10 located beneath the transparent reticle 20 to receive an image 50. In step 103 the processor 13 sends a command to a frame grabber 12 to acquire an image 50, comprising pixel values from the camera 10. The method then proceeds to step 104 and processes the pixel values with a processor 13.

Figure 2B:
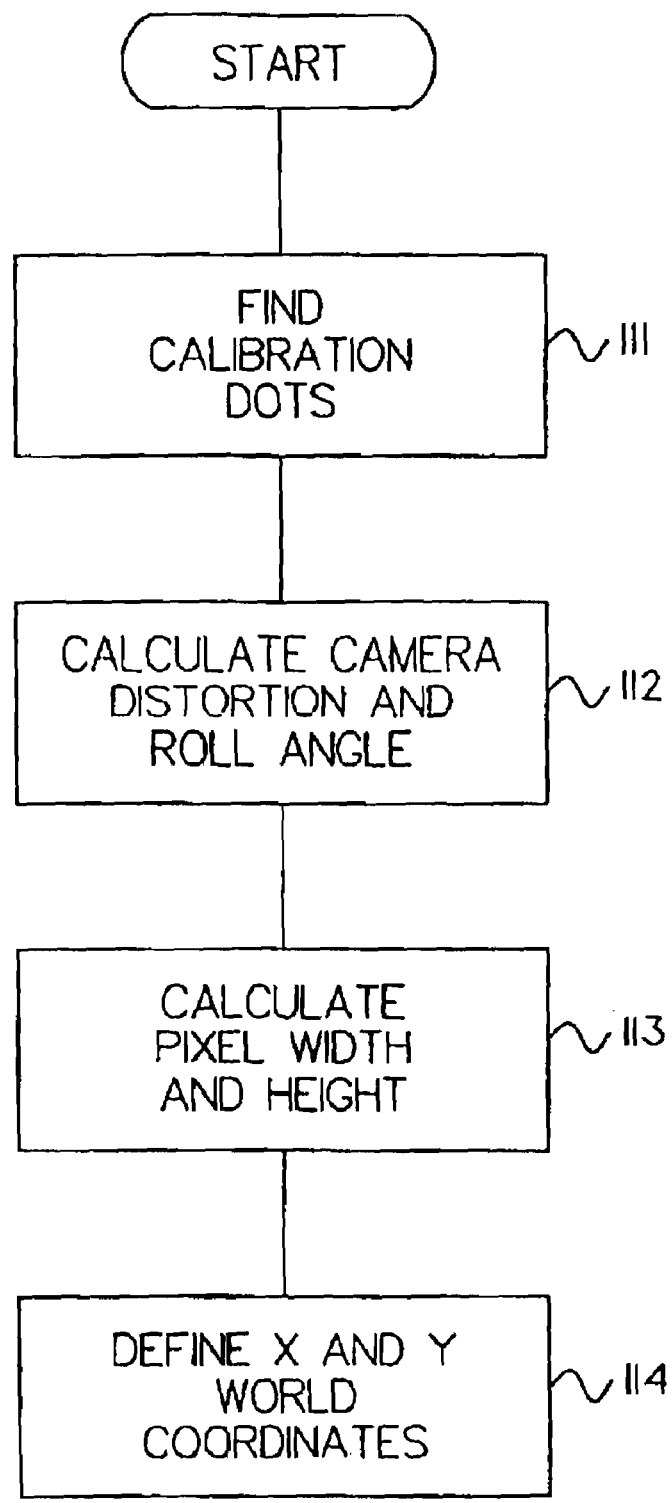
FIG. 2B shows a flow chart of a method of the invention used for determining the state values, and the X and Y world coordinates, of the bottom view of the system.

FIG. 2B shows a flow diagram for determining the state values of the bottom view of the system. In step 111 the method begins by finding the dots 52 in image 50, corresponding to the calibration dots 24. The processor finds a dimension and position for each dot visible in image 50 in subpixel values using well known grayscale methods and stores these values in memory 14. By comparing these results to known values stored in memory, the processor calculates the missing state values for the bottom calibration in steps 112 and 113. In step 112 the processor 13 calculates the optical distortion of lens 11 and the camera roll angle with respect to the dot pattern 22. Step 113 calculates the pixel width and pixel height by comparing the subpixel data of dots 52 with the known dimensions of the precision dot pattern 22. The pixel aspect ratio is determined from the pixel width and pixel height. In step 114 the processor defines the X and Y world coordinates and the Z=0 plane from the image 50 of the precision dot pattern 22. The processor then stores these results in memory. These results provide conversion factors for use during analysis to convert pixel values to world values.

Figure 2C:
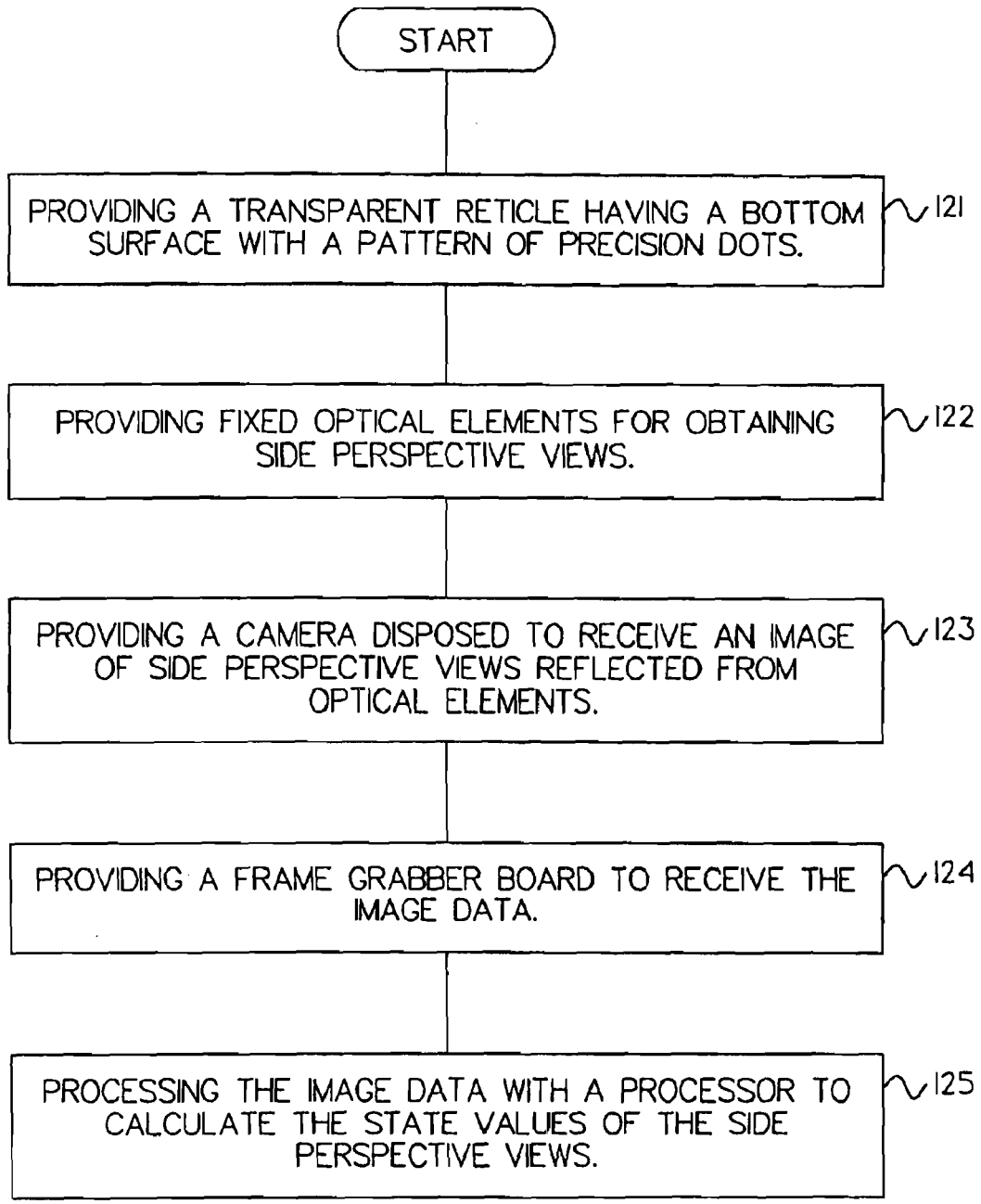
FIG. 2C shows a flow chart of a method of the invention used for calibration of the side perspective views.

FIG. 2C shows a flow diagram for the calibration of the side perspective views of the system. The method starts in step 121 by providing a transparent reticle 20 having a bottom surface containing a dot pattern 22, comprising precision dots 24 of known dimensions and spacing. The method in step 122 provides fixed optical elements 30, 32, 34, 36 and 38 to reflect two perspective images of the precision dot pattern 22 into camera 15. The method in step 123 provides a camera 15 located to receive an image 60. In step 124 the processor 13 sends a command to a frame grabber 12 to acquire an image 60, comprising pixel values from the camera 15. The method then proceeds to step 125 and processes the pixel values with a processor 13.

Figure 2D:
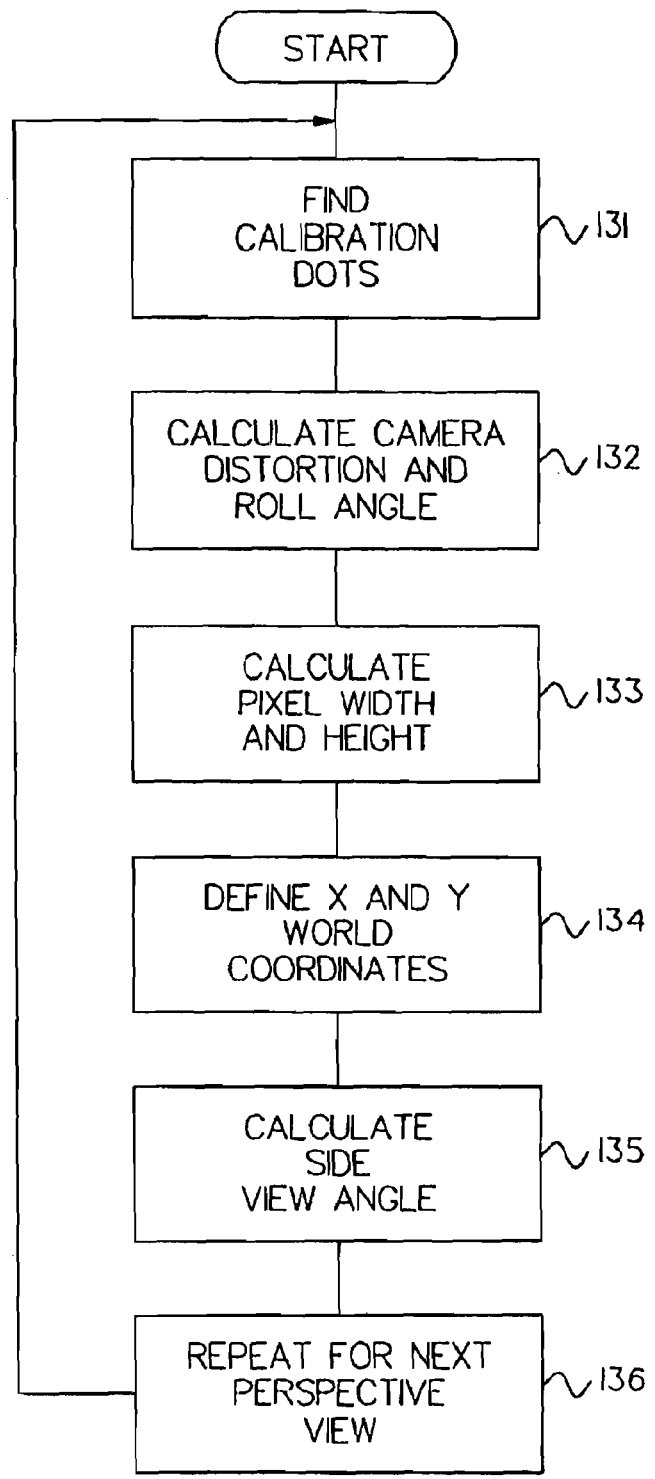
FIG. 2D shows a flow chart of a method of the invention used for determining the state values of the side perspective views of the system.

FIG. 2D shows a flow diagram for determining the state values of the side perspective views of the system. In step 131 the method begins by finding dots 62 in image 60, corresponding to the calibration dots 24. The processor finds a dimension and position for each dot visible, comprising the group of dots 62, in image 60 for a first side perspective view in subpixel values and stores these values in memory 14. By comparing these results to known values stored in memory, the processor calculates the missing state values for a side perspective view, comprising the group of dots 62, in steps 132 and 133. In step 132 the processor 13 calculates the optical distortion of lens 16 and the camera roll angle with respect to the dot pattern 22. In step 133 the processor 13 calculates the pixel width and pixel height by comparing the subpixel data of dots 62 with the known dimensions of the precision dots 24. The pixel aspect ratio is determined from the pixel width and pixel height. In step 134 the processor defines the X and Y world coordinates and the Z=0 plane from the dots 62 in image 60 of the dot pattern 22. The processor then stores these results in memory. These results provide conversion factors for use during analysis to convert pixel values to world values. In step 135 the method of the invention computes the side view angle. In step 136 the method is repeated for a second side perspective view using the dots 66 in image 60.

Figure 2E:
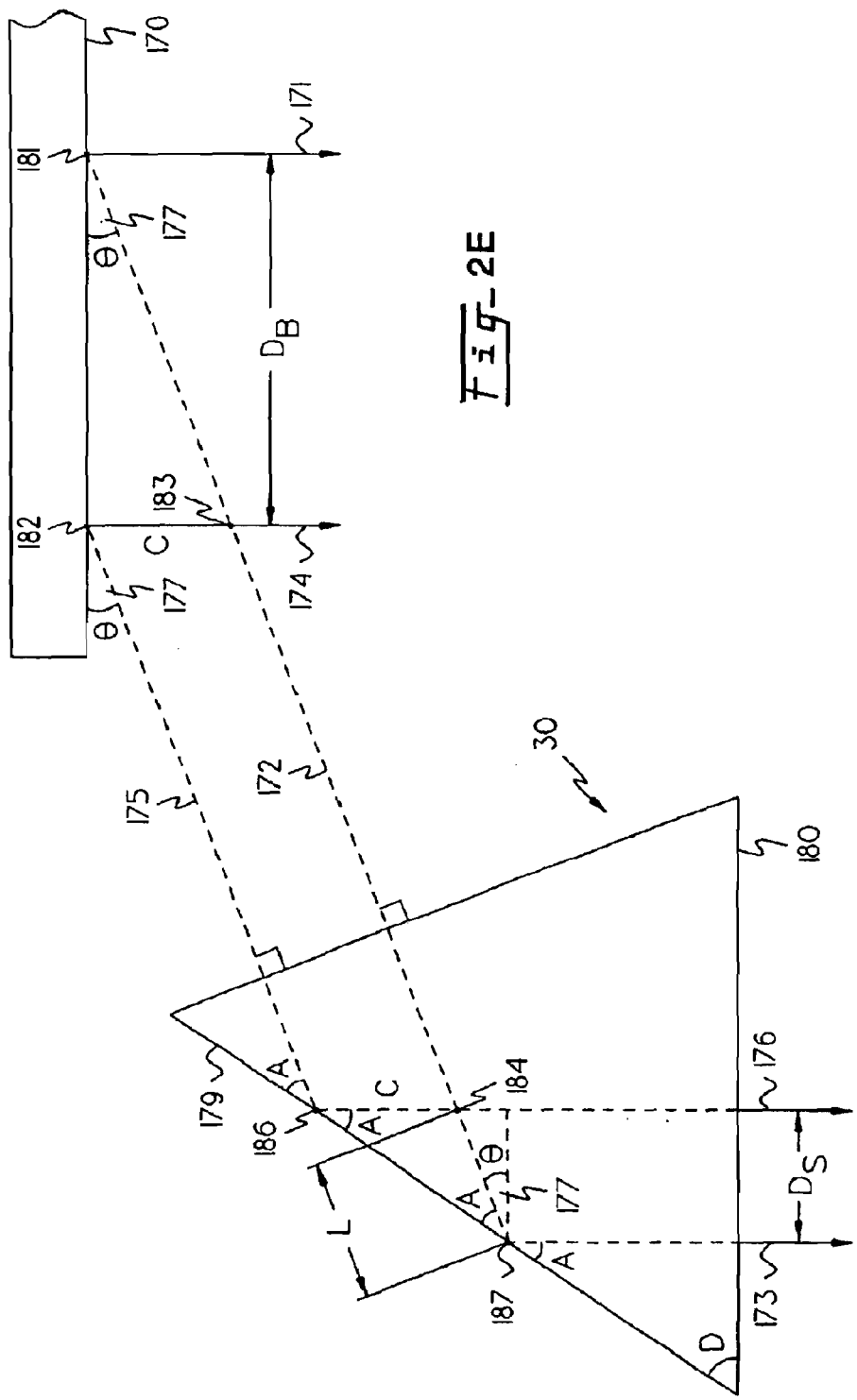
FIG. 2E shows the relationship of a side perspective angle to the ratio of the perspective dimensions to the non-perspective dimensions.

FIG. 2E shows the relationship of a side perspective angle to the ratio of the perspective dimension to the non-perspective dimension. Ray 171, 172, and 173 defining point 181 is parallel to ray 174, 175 and 176 defining point 182. Point 181 and point 182 lie on a plane 170 parallel to a plane 180. The intersection of ray 175 and ray 176 define point 186. The intersection of ray 176 and ray 172 define point 184. The intersection of ray 173 and ray 172 define point 187. The intersection of ray 174 and ray 172 define point 183. The reflecting plane 179 intersecting plane 180 at an angle D is defined by ray 172 and ray 175 and the law of reflectance. Ray 172 and ray 175 intersect plane 170 at an angle 177. Referring to FIG. 2E it can be shown:

$$\tan \theta = C/D_B$$

$$C/\sin A = L/\sin A \text{ Therefore: } C=L$$

$$\cos \theta = D_S/L = D_S/C$$

$C = D_S / \cos\theta$

Figure 2F:
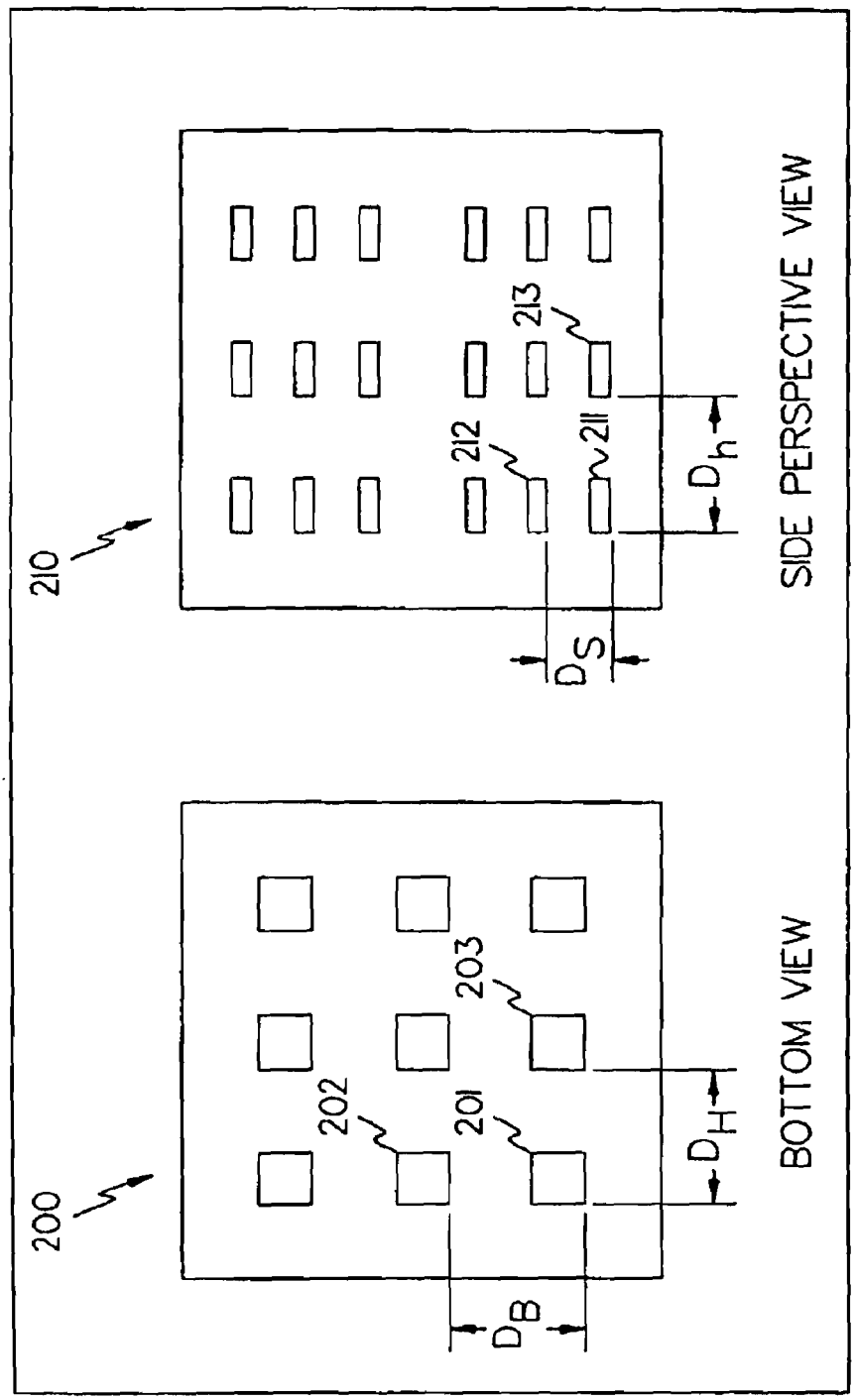
FIG. 2F shows a bottom view and a side perspective view of precision dots used in the method for determining a side perspective view angle.

Substituting:

$\tan\theta = (D_S/\cos\theta)/D_B = D_S/D_B \cos\theta$ $(\tan\theta)(\cos\theta) = D_S/D_B \sin\theta$ $\theta = \arcsin(D_S/D_B)$ FIGS. 2F show a bottom view and a side perspective view of precision dots used in the method for determining a side perspective view angle 177 as shown in FIG. 2E of the system. A bottom view image 200 comprising precision dots 201, 202 and 203 of known spacing and dimensions from the calibration method described earlier can be used to provide a reference for determination of a side perspective view angle 177. The value $D_H$ and $D_B$ are known from the bottom view calibration. A side perspective view image 210 comprising precision dots 211, 212 and 213, corresponding to bottom view dots 201, 202 and 203 respectively, of known spacing and dimensions $D_S$ and $D_h$ from the calibration method described earlier, can be used to determine the side view perspective angle. The ratio of $(D_h/D_H)$ from the bottom image 200 and the side perspective image 210 can be used in the bottom view to calibrate $D_B$ in the same units as the side perspective view as follows:

$D_{Bcal} = D_B(D_h/D_H)$

Figure 3A:
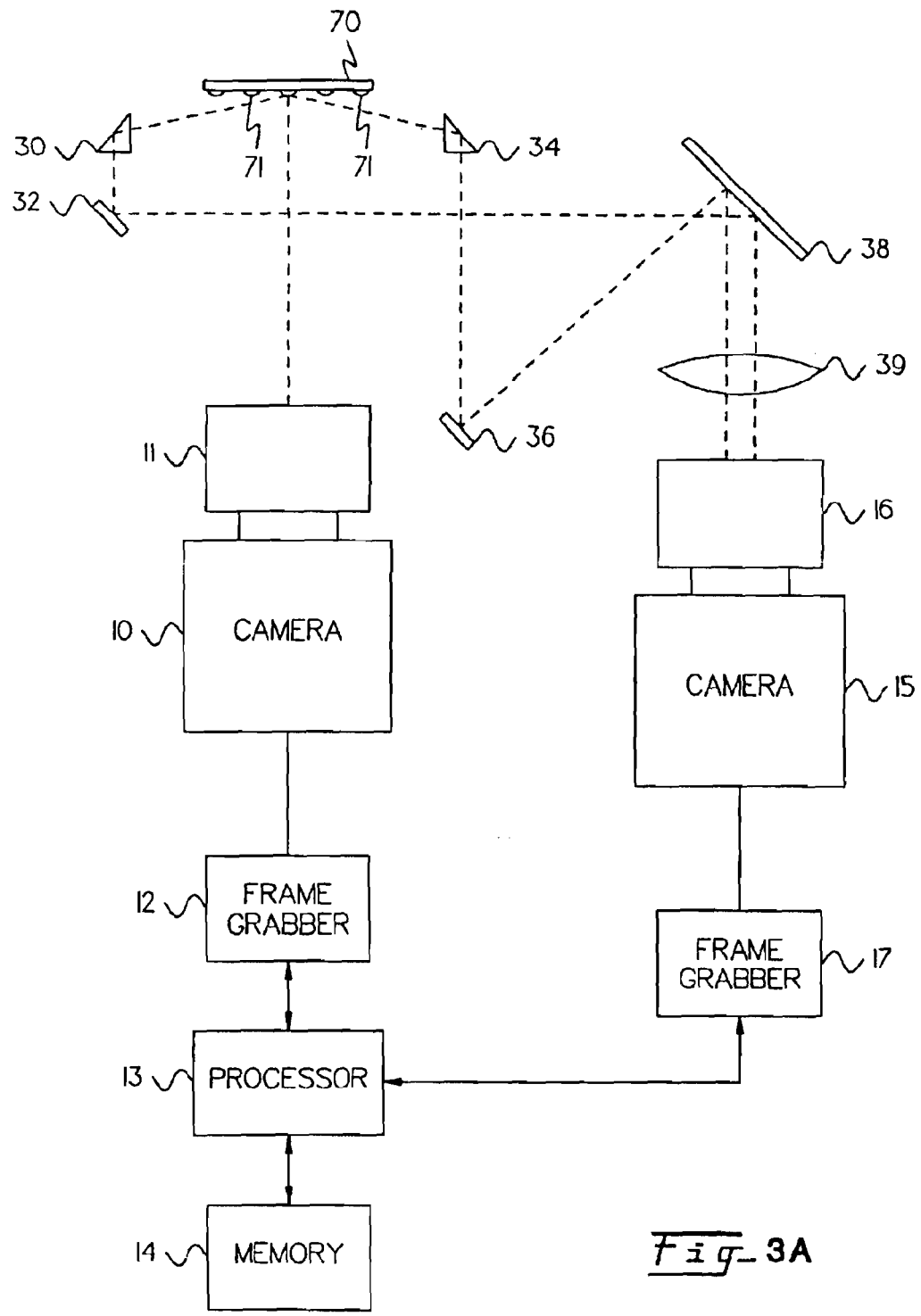
FIG. 3A shows the apparatus of the invention for part inspection.
Figure 8B:
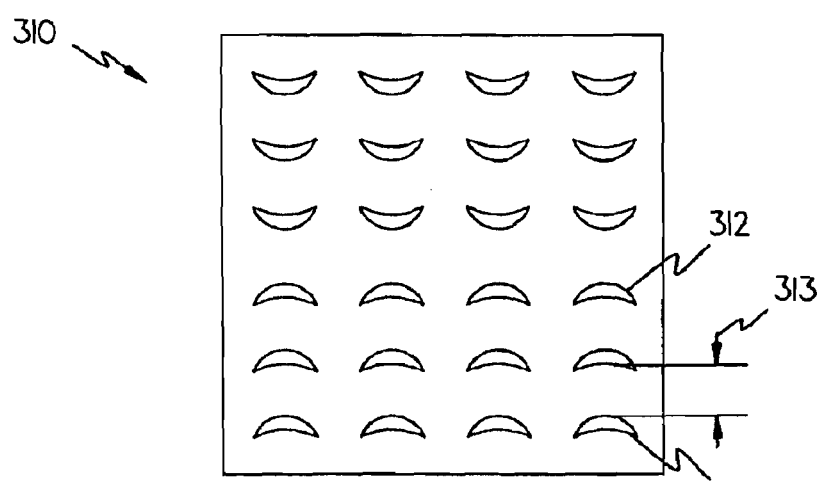
FIG. 8B shows a side perspective image of the balls on a BGA, magnified in one dimension.

Substituting into the equation for the side perspective view angle 177 described earlier yields:

$\theta = \arcsin(D_S/D_B) = \arcsin(D_S/D_{Bcal})$ $\theta = \arcsin(D_S D_H / D_B D_h)$ FIG. 3A shows the apparatus of the invention for a three dimensional inspection of the balls of a ball grid array. The apparatus of the invention includes a part 70 to be inspected. The apparatus further includes a camera 10 with a lens 11, located below the central area of part 70, to receive a bottom image 80, described in conjunction with FIG. 3B, of part 70. The camera 10 is connected to a frame grabber board 12 to receive the image 80. The frame grabber board 12 provides an image data output to a processor 13 to perform a two dimensional inspection as described in conjunction with FIG. 3A. The processor 13 may store an image in memory 14. The apparatus of the invention obtains an image of a pair of side perspective views with a camera 15 and a lens 16. The camera 15 is located to receive an image 90, comprising a pair of side perspective views, described in conjunction with FIG. 3B and utilizing fixed optical elements 30, 32 and 38 for a first side perspective view and fixed optical elements 34, 36 and 38 for a second side perspective view. In one embodiment of the invention, the apparatus may contain a nonlinear optical element 39 to magnify the side perspective image 60 in one dimension as shown in FIG. 8B. In another embodiment of the invention optical element 38 may be the nonlinear element. The fixed optical elements 30, 32, 34, 36 and 38 may be mirrors or prisms. As will be appreciated by those skilled in the art additional optical elements may be incorporated without deviating from the spirit and scope of the invention. The camera 15 is connected to a frame grabber board 17 to receive the image 90. The frame grabber board 17 provides an image data output to a processor 13 to calculate the Z position of the balls, described in conjunction with FIG. 3B. The processor 13 may store an image in memory 14.

Figure 3B:
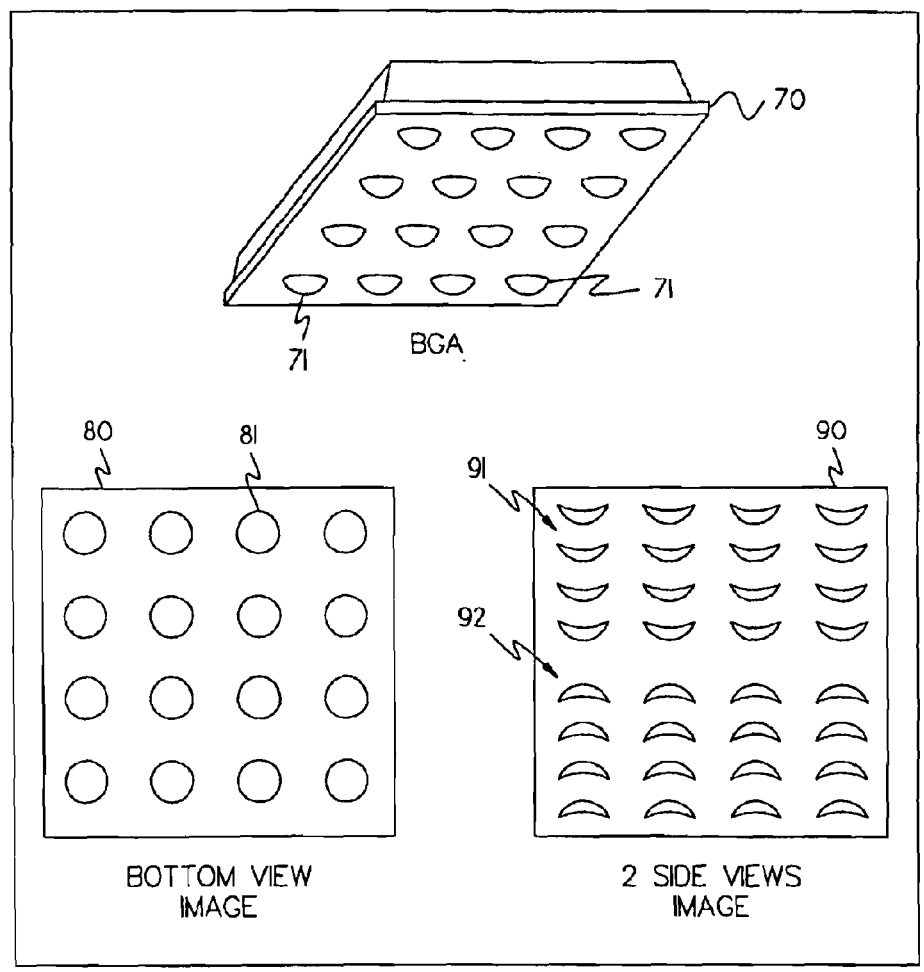
FIG. 3B shows example images of a part acquired by the system.

FIG. 3B show an example image 80 from camera 10 and an example image 90 from camera 15 acquired by the system.

The image 80 shows the bottom view of the balls located on the bottom surface of a part 70. The image 90 shows two side view perspectives of the balls located on part 70. A first side perspective view in image 90 contains images of balls 91 and is obtained by the reflection of the image of the part 70 off of fixed optical elements 30, 32 and 38 into camera 15. A second side perspective view in image 90 contains images of balls 92 and is obtained by the reflection of the image of the part 70 off of fixed optical elements 34, 36 and 38 into camera 15. Optical element 36 is positioned to adjust the optical path length of a second side perspective view to equal the optical path length of a first side perspective view. In one embodiment of the invention, the maximum depth of focus of a side perspective view just includes an area of the part including the center row of balls. This allows for a fixed focus system to inspect larger parts, with one perspective view imaging at least half of the part and the second perspective view imaging at least the other half of the part. Those skilled in the art will realize that any number of perspective views can be utilized by the invention. In another embodiment of the invention, all of the balls are in focus from both side perspective views resulting in two perspective views for each ball. This permits two Z calculations for each ball as shown in conjunction with FIGS. 10A and 10B.

Figure 4:
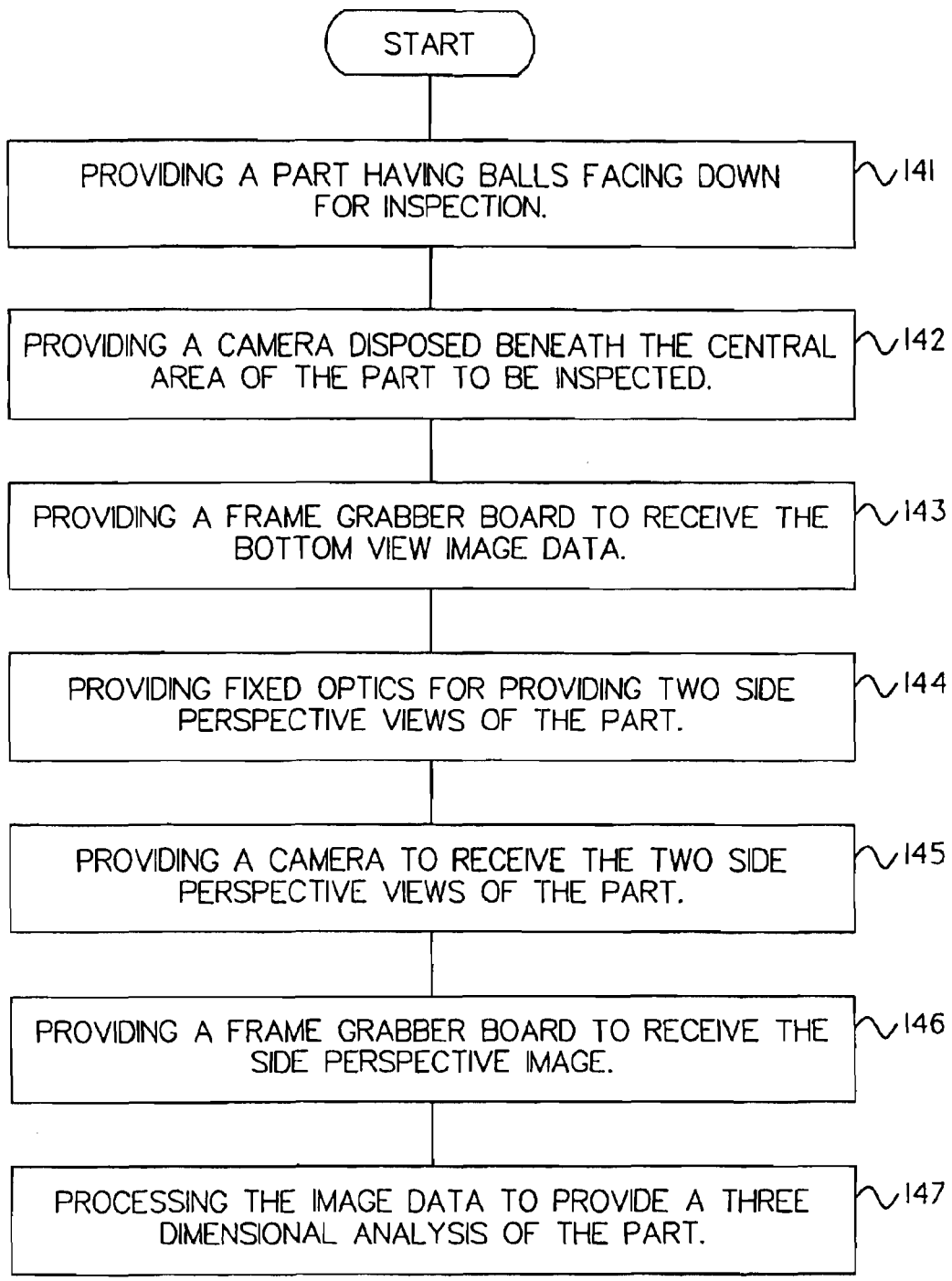
FIG. 4 shows a method of the invention for the three dimensional inspection of balls on a ball grid array.

FIG. 4 shows a flow diagram for the three dimensional inspection of balls on a ball grid array. The method starts in step 141 by providing a part 70 having balls 71 facing down. The method in step 142 provides a camera 10 located beneath the part 70 to receive an image 80. In step 143 a frame grabber 12 is provided to receive the image 80 from camera 10. In step 144, fixed optical elements are provided for obtaining two side perspective views of the part 70. A first optical path is provided by optical elements 30, 32 and 38. A second optical path is provided by optical elements 34, 36 and 38. A second camera 15 receives an image 90 of two side perspective views in step 145. In step 146 a second frame grabber board 17 is provided to receive the image 90 from camera 15. A processor 13 sends a command to frame grabbers 12 and 17 to acquire images 80 and 90 comprising pixel values from cameras 10 and 15. The method then proceeds to step 147 and processes the pixel values with a processor 13 to obtain three dimensional data about part 70.

The invention contemplates the inspection of parts that have ball shaped leads whether or not packaged as a ball grid array. The invention also contemplates inspection of leads that present a generally curvilinear profile to an image sensor.

Figure 5A:
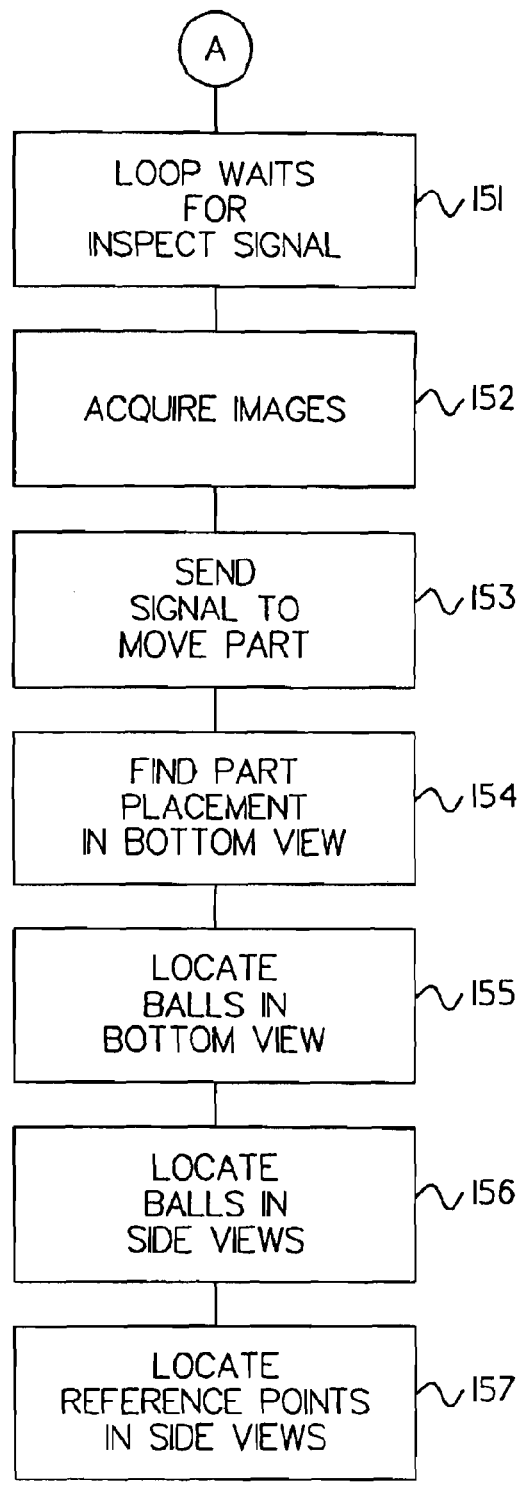
FIGS. 5A and 5B together show a flow chart of the three dimensional inspection of the invention.
Figure 5B:
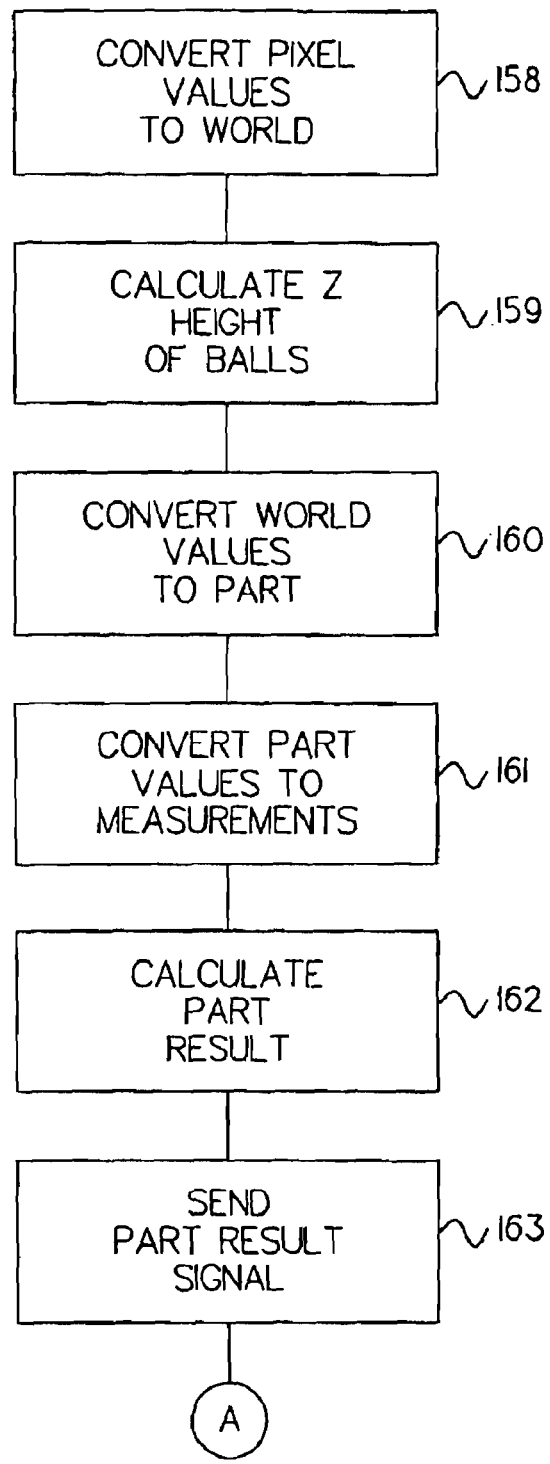

FIGS. 5A and 5B together show a flow chart of the three dimensional inspection method of the invention. The process begins in step 151 by waiting for an inspection signal. When the signal changes state, the system initiates the inspection. The processor 13 sends a command to frame grabber boards 12 and 17 to acquire images 80 and 90 respectively of part 70 having balls 71. In step 152, camera 10 captures an image 80 comprising pixel values and camera 15 captures an image 90 comprising pixel values and the processor stores the images in memory 14. The images comprise information from both a bottom view and two side perspective views as shown in FIG. 3B. In step 153, the inspection system sends a signal to a part handler shown in FIG. 9 to allow the part handler to move the part out of the inspection area and allows the next part to be moved into the inspection area. The handler may proceed with part placement while the inspection system processes the stored image data.

The inspection system processes the pixel values of the stored image 80 in step 154 to find a rotation, and X placement and Y placement of the part relative to the world X and Y coordinates. The processor determines these placement values finding points on four sides of the body of the part. In step 155, the processor employs a part definition file that contains values for an ideal part.

By using the measurement values from the part definition file and the placement values determined in step 154, the processor calculates an expected position for each ball of the part for the bottom view contained in image 80.

The processor employs a search procedure on the image data to locate the balls 81 in image 80. The processor then determines each ball's center location and diameter in pixel values using grayscale blob techniques as described in FIG. 7A. The results are stored in memory 14.

The processor proceeds in step 156 to calculate an expected position of the center of each ball in both side perspective views in image 90 using the known position of each side view from calibration. The processor employs a subpixel edge detection method described in FIG. 7B to locate a reference point on each ball in step 157. The results are stored in memory 14.

Now refer to FIG. 5B. In step 158 the processor converts the stored pixel values from steps 154 and 157 into world locations by using pixel values and parameters determined during calibration. The world locations represent physical locations of the balls with respect to the world coordinates defined during calibration.

In step 159 the Z height of each ball is calculated in world coordinates in pixel values. The method proceeds by combining the location of the center of a ball from the bottom view 80 with the reference point of the same ball from a side perspective view in image 90 as described in FIGS. 6A and 6B. The processor then converts the world values to part values using the calculated part rotation, and X placement and Y placement in step 160 to define part coordinates for the ideal part. The part values represent physical dimensions of the balls such as ball diameter, ball center location in X part and Y part coordinates and ball height in Z world coordinates.

In step 161 these part values are compared to the ideal values defined in the part file to calculate the deviation of each ball center from its ideal location. In one example embodiment of the invention the deviation values may include ball diameter in several orientations with respect to the X and Y part coordinates, ball center in the X direction, Y direction and radial direction, ball pitch in the X direction and Y direction and missing and deformed balls. The Z world data can be used to define a seating plane, using well known mathematical formulas, from which the Z dimension of the balls with respect to the seating plane can be calculated. Those skilled in the art will recognize that there are several possible definitions for seating planes from the data that may be used without deviating from the spirit and scope of the invention.

In step 162 the results of step 161 are compared to predetermined thresholds with respect to the ideal part as defined in the part file to provide an electronic ball inspection result. In one embodiment the predetermined tolerance values include pass tolerance values and fail tolerance values from industry standards. If the measurement values are less than or equal to the pass tolerance values, the processor assigns a pass result for the part. If the measurement values exceed the fail tolerance values, the processor assigns a fail result for the part. If the measurement values are greater than the pass tolerance values, but less than or not equal to the fail tolerance values, the processor designates the part to be reworked. The processor reports the inspection result for the part in step 163, completing part inspection. The process then returns to step 151 to await the next inspection signal.

Figure 6A:
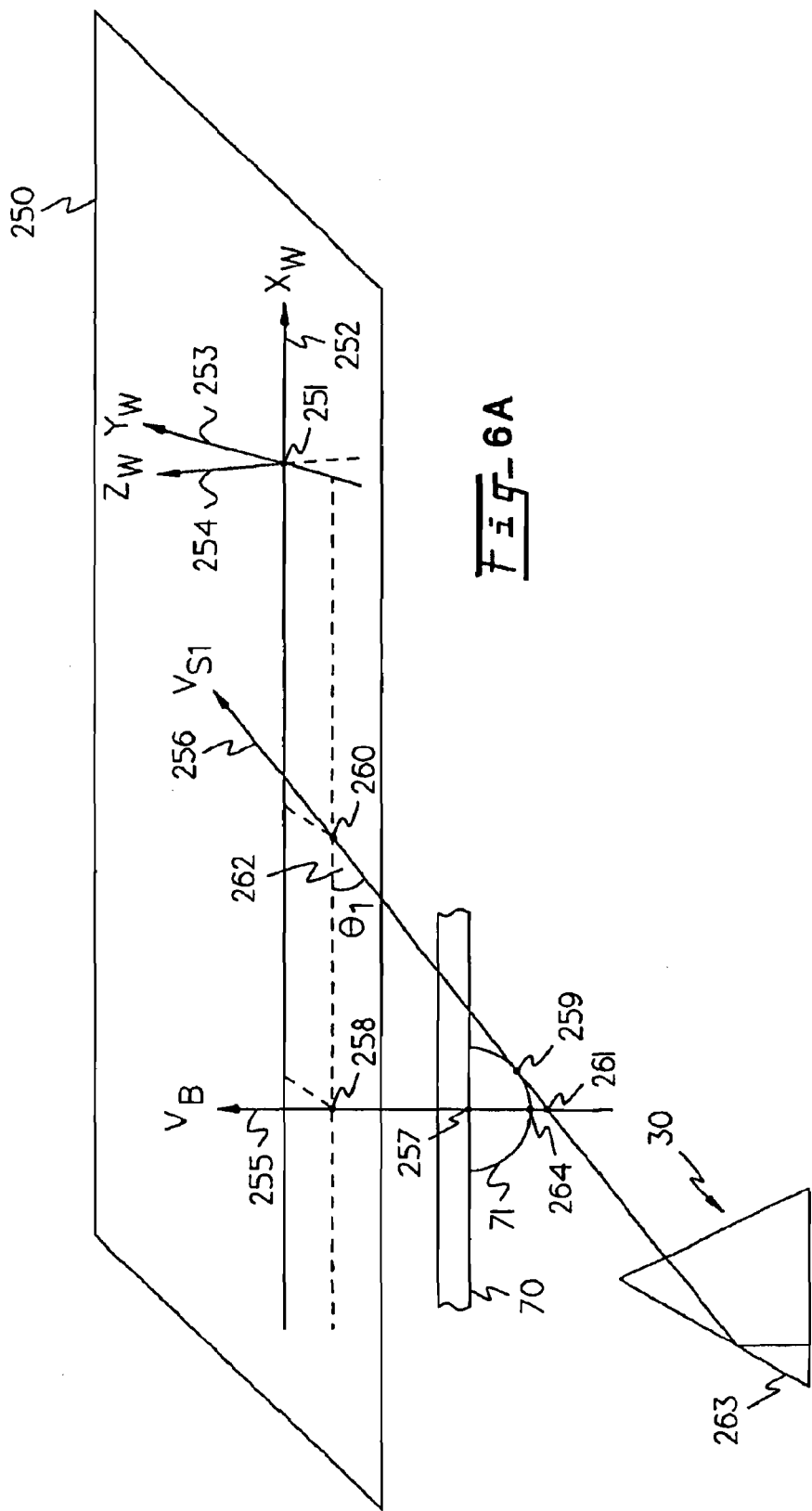
FIGS. 6A and 6B show an example ball of a ball grid array and associated geometry used in a method of the invention for determining the Z position of the ball.
Figure 6B:
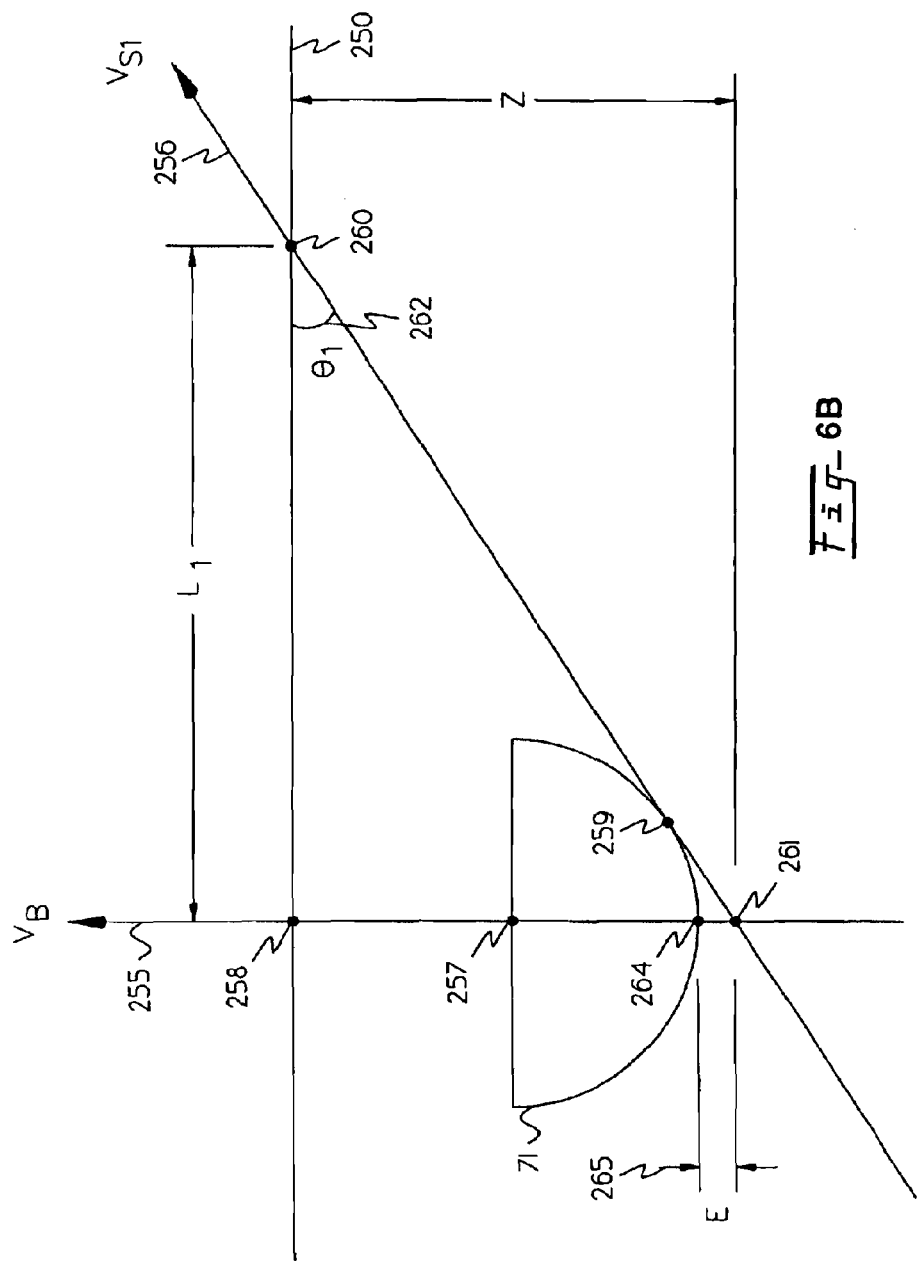

FIGS. 6A and 6B show an example ball of a ball grid array and associated geometry used in a method of the invention for determining the Z position of the ball. The method determines the Z position of a ball with respect to the world coordinates defined during calibration. Using parameters determined from the calibration procedure as shown in FIGS. 2B and 2D to define a world coordinate system for the bottom view and the two side perspective views, comprising world coordinate plane 250 with world coordinate origin 251 and world coordinate axis X 252, Y 253 and Z 254 shown in FIG. 6A, and a pair of images 80 and 90 as shown in FIG. 3B, the processor computes a three dimensional location.

Now refer to FIG. 6A. The processor locates a point 258 on the world plane 250 determined by a bottom view ray 255 passing through the center 257 of a ball 71 on a part 70. The processor locates a side perspective view point 260 on the world plane 250 determined by a side perspective view ray 256 intersecting a ball reference point 259 on ball 71 and intersecting the bottom view ray 255 at a virtual point 261. Ray 256 intersects the world plane 250 at an angle 262 determined by the reflection of ray 256 off of the back surface 263 of prism 30. The value of angle 262 was determined during the calibration procedure.

Now refer to FIG. 6B. The distance $L_1$ is calculated by the processor as the difference between world point 258, defined by the intersection of ray 255 with the Z=0 world plane 250, and world point 260, defined by the intersection of ray 256 and the Z=0 world plane 250. The value Z is defined as the distance between world point 261 and 258 and is related to $L_1$ as follows:

$$\tan \theta_1 = Z/L_1$$

$$Z = L_1 \tan \theta_1$$

Z can be computed by processor 13 since the angle 262 is known from calibration. The offset E 265 is the difference between the virtual point 261 defined by the intersection of ray 255 and ray 256 and the crown of ball 71 at point 264, defined by the intersection of ray 255 with the crown of ball 71, and can be calculated from the knowledge of the angle 262 and the ideal dimensions of the ball 71. The final value of Z for ball 71 is:

$$Z_{Final} = Z - E$$

Figure 7A:
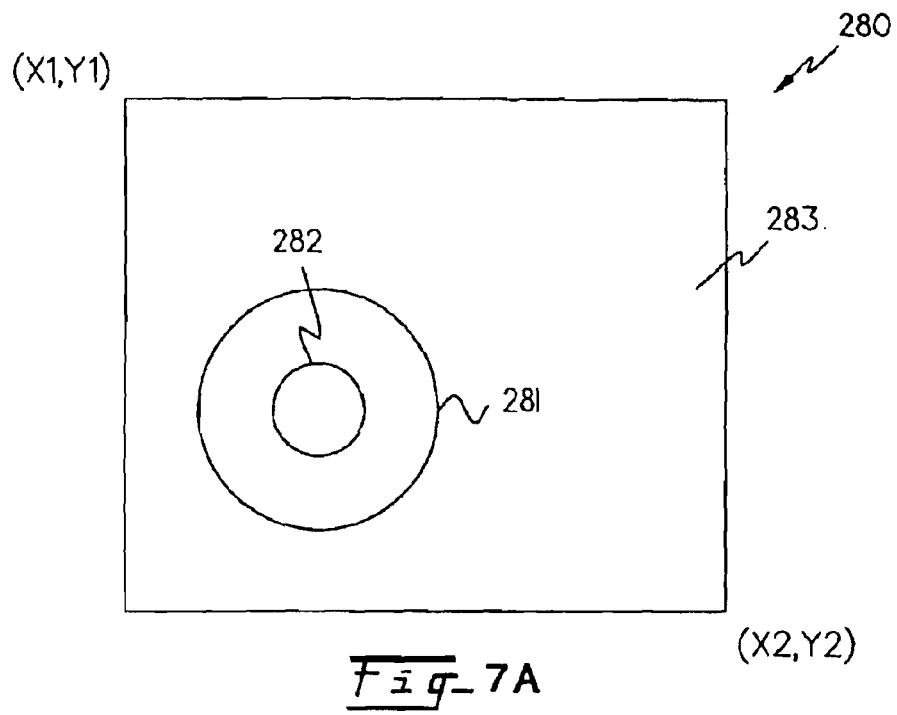
FIG. 7A shows one example of an image used in the grayscale blob method of the invention.

FIG. 7A shows one example of an image used in the grayscale blob method of the invention. The image processing method finds the location and dimensions of a ball 71 from a bottom image 80. From the expected position of a ball 71, a region of interest in image 80 is defined as (X1, Y1) by (X2, Y2). The width and height of the region of interest are large enough to allow for positioning tolerances of part 70 for inspection. Due to the design of the lighting for the bottom view (e.g., a ring light), the spherical shape of balls 71 of part 70 present a donut shaped image where the region 281, including the perimeter of the ball 71, comprises camera pixels of higher grayscale values and where the central region 282 comprises camera pixels of lower grayscale values. The remainder 283 of the region of interest 280 comprises camera pixels of lower grayscale values.

In one embodiment of the invention the processor 13 implements image processing functions written in the C programming language.

The C language function "FindBlobCenter", as described below, is called to find the approximate center of the ball 71 by finding the average position of pixels that are greater than a known threshold value. Using the coordinates of the approximate center of the ball 71, the region 282 of lower grayscale pixel values can be converted to higher grayscale values by calling the C language function "FillBallCenter", as described below. The exact center of the ball 71 can be found by calling the C language function "FindBallCenter" which also returns an X world and Y world coordinate. The diameter of the ball 71 can be calculated by the C language function, "Radius=sqrt(Area/3.14)". The area used in the diameter calculation comprises the sum of pixels in region 281 and 282.

Figure 7B:
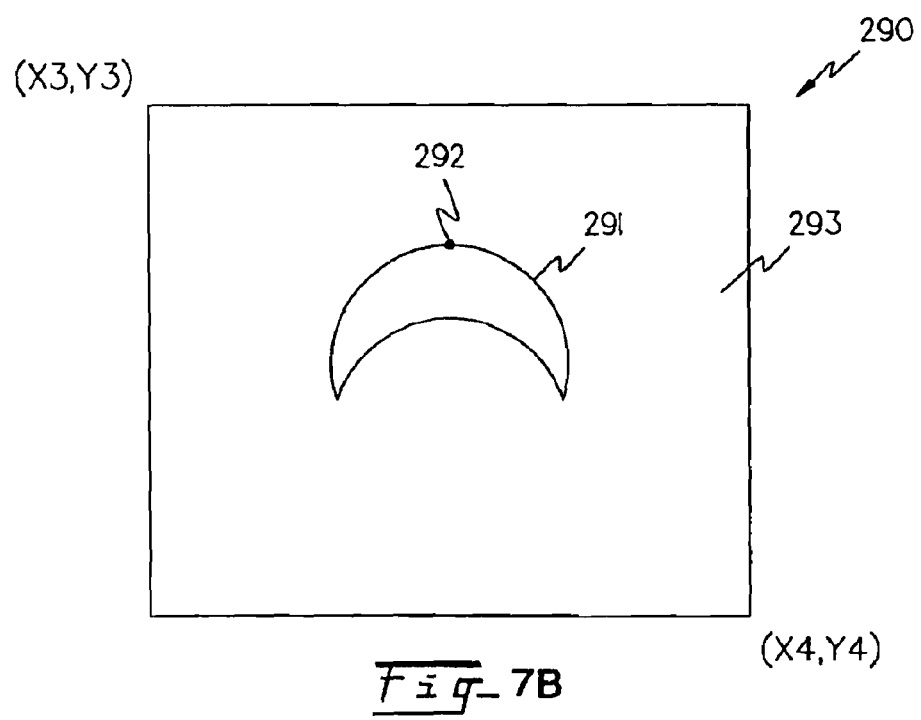
FIG. 7B shows one example of an image used with the method of the invention to perform a subpixel measurement of the ball reference point.

FIG. 7B shows one example of an image used with the method of the invention to perform a subpixel measurement of the ball reference point. The method of the invention finds a reference point on a ball 71 in an image 90 of a side perspective view as shown in FIG. 3B. From the expected position of a ball 71, a region of interest 290 in image 80 is defined as (X3, Y3) by (X4, Y4). The width and height of the region of interest are large enough to allow for positioning tolerances of part 70 for inspection. Due to the design of the lighting for a side perspective view (e.g., using a light diffuser), the spherical shape of balls 71 of part 70 present a crescent shaped image 291 comprising camera pixels of higher grayscale values and where the remainder 293 of the region of interest 290 comprises camera pixels of lower grayscale values.

The C language function "FindBlobCenter" is called to compute the approximate center of the crescent image 291 by finding the average position of pixels that are greater than a known threshold value. Using the coordinates of the approximate center of the crescent image 291, the C language function "FindCrescentTop" is called to determine the camera pixel, or seed pixel 292 representing the highest edge on the top of the crescent. The camera pixel coordinates of the seed pixel are used as the coordinates of a region of interest for determining the subpixel location of the side perspective ball reference point.

One example of grayscale blob analysis and reference point determination implemented in the C language is presented as follows:

```
////////////////////////////////////////////////////////
//
// FindBlobCenter - finds the X,Y center of the pixels that have
    a value greater than THRESHOLD in the region (x1,y1) to (x2,y2)
////////////////////////////////////////////////////////
//
long FindBlobCenter(int x1,int y1,int x2,int y2, double* pX,double* pY)
{
    int x,y;
    long Found = 0;
    long SumX = 0;
    long SumY = 0;
    for (x=x1;x<=x2;x++)
    {
        for (y=y1;y<=y2;y++)
        {
            if (Pixel [x] [y] > THRESHOLD)
            {
                SumX += X;
                SumY += y;
                Found ++;
            }
        }
    }
    if (Found > 0)
    {
        *pX = (double)SumX / (double)Found;
        *pY = (double)SumY / (double)Found;
    }
    return Found;
}
////////////////////////////////////////////////////////
//
// FillBallCenter - fills the center of the BGA "donut"
//
```

-continued

```
void FillBallCenter(double CenterX,double CenterY,double Diameter)
////////////////////////////////////////////////////////
{
    int x,y;
    int x1 = (int) (CenterX – Diameter / 4.0);
    int x2 = (int) (CenterX + Diameter / 4.0);
    int y1 = (int) (CenterY – Diameter / 4.0);
    int y2 = (int) (CenterY + Diameter / 4.0);
    for (x=x1;x<=x2;x++)
    {
        for (y=y1;y<=y2;y++)
        {
            Pixel [x] [y] = 255;
        }
    }
}
////////////////////////////////////////////////////////
//
// FindBallCenter - finds the X,Y center of the a BGA ball
//     using the grayscale values
////////////////////////////////////////////////////////
//
long FindBallCenter(int x1,int y1,int x2,int y2, double* pX,double* pY,
                    double* pRadius)
{
    int x,y;
    long Found = 0;
    long Total = 0;
    long SumX = 0;
    long SumY = 0;
    for (x=x1;x<=x2;++)
    {
        for (y=y1;y<=y2;y++)
        {
            if (Pixel [x] [y] > THRESHOLD)
            {
                SumX += x*Pixel [x] [y];
                SumY += y*Pixel [x] [y];
                Total += Pixel [x] [y];
                Found ++;
            }
        }
    }
    if (Found > 0)
    {
        *pX = (double)SumX / (double)Total;
        *pY = (double)SumY / (double)Total;
        *pRadius = sqrt((double)Found / 3.14159279);
    }
    return Found;
}
////////////////////////////////////////////////////////
//
// FindCresentTop - finds the X,Y top position of a BGA cresent
////////////////////////////////////////////////////////
//
void FindCresentTop(int CenterX,int CenterY,int Diameter,
int* pX,int* pY)
{
    int x,y,Edge,Max,TopX,TopY;
    int x1 = CenterX – Diameter / 2;
    int x2 = CenterX + Diameter / 2;
    int y1 = CenterY – Diameter / 2;
    int y2 = CenterY;
    *pY = 9999;
    for (x=x1;x<=x2;x++)
    {
        Max = –9999;
        for (y=y1;y<=y2;y++)
        {
            Edge = Pixel [x] [y] – Pixel [x] [y–1];
            if (Edge > Max)
            {
                Max = Edge;
                TopY = y;
                TopX = x;
            }
        }
        if(TopY < *pY)
```

-continued

```
    {
        *pX = TopX;
        *pY = TopY;
    }
}
```

(c) 1997 Scanner Technologies Inc.

FIG. 8A shows a side perspective image of the calibration pattern magnified in one dimension. FIG. 8A shows a side perspective image 300 of a reticle calibration pattern where the space 303 between dot 301 and dot 302 is magnified, increasing the number of lower value grayscale pixels when compared to a non magnified image.

FIG. 8B shows a side perspective image of the balls on a BGA, magnified in one dimension. In FIG. 8B a side perspective image 310 of two views are shown where the space 313 between ball image 311 and ball image 312 is magnified, increasing the number of lower value grayscale pixels when compared to a non magnified image. The increased number of lower grayscale value pixels allows for the successful application of the subpixel algorithm.

In another embodiment of the invention, the method and apparatus disclosed herein is a method and apparatus for calibrating the system by placing a pattern of calibration dots of known spacing and dimensions on the bottom plane of a calibration reticle and for providing for two side perspective views of each ball for the three dimensional inspection of parts. From the precision dots the missing state values of the system are determined allowing for three dimensional inspection of balls on BGA devices or balls on wafers or balls on die.

FIG. 9 shows an example apparatus for presenting a BGA to the system for inspection. An overhead light reflective diffuser includes a vacuum cup assembly 6. The vacuum cup assembly may attach to a BGA part 70 having balls 71 and suspend the BGA part 70 below the overhead light reflective diffuser 5.

Figure 10A:
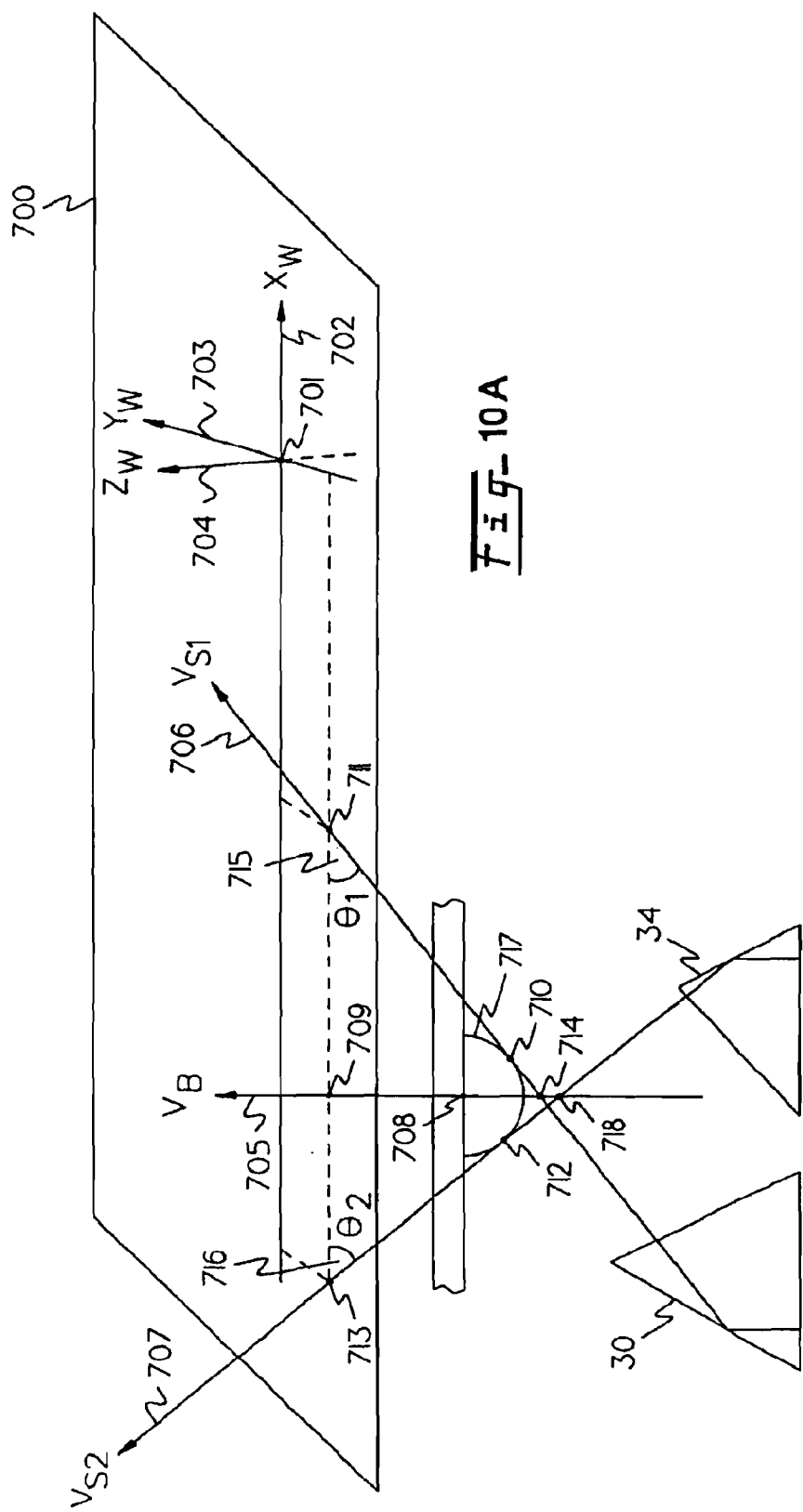

FIGS. 10A and 10B show an example ball on a ball grid array and associated geometry for use with the method of the invention for determining the Z position of a ball with respect to the world coordinates defined during calibration, using two perspective views for each ball. Using parameters determined from the calibration procedure as shown in FIGS. 2B and 2D to define a world coordinate system for the bottom view and the two side perspective views, comprising world coordinate plane 700 with world coordinate origin 701 and world coordinate axis X 702, Y 703 and Z 704 shown in FIG. 10A and FIG. 10B, and a pair of images 80 and 90 as shown in FIG. 3B, the processor computes a three dimensional location.

Now refer to FIG. 10A. The processor locates a point 709 on the world plane 700 determined by a bottom view ray 705 passing through the center 708 of a ball 717. The processor locates a first side perspective view point 711 on the world plane 700 determined by a side view ray 706 intersecting a ball reference point 710 on ball 717 and intersecting the bottom view ray 705 at a virtual point 714. Ray 706 intersects the world plane 700 at an angle 715 determined by the reflection of ray 706 off of the back surface of prism 30. The value of angle 715 was determined during the calibration procedure. The processor locates a second side perspective view point 713 on the world plane 700 determined by a side view ray 707 intersecting a ball reference point 712 on ball 717 and intersecting the bottom view ray 705 at a virtual point 718. Ray 707 intersects the world plane 700 at an angle 716 determined by the reflection of ray 707 off of the back surface of prism 34. The value of angle 716 was determined during the calibration procedure.

Now refer to FIG. 10B. The distance L1 is calculated by the processor as the distance between world point 709 and world point 711. The distance L2 is calculated by the processor as the distance between world point 713 and world point 709. The value $Z_1$ is defined as the distance between world point 714 and 709 and is related to $L_1$ as follows:

$$\tan \theta_1 = Z_1/L_1$$

$$Z_1 = L_1 \tan \theta_1$$

The value $Z_2$ is defined as the distance between world point 718 and 709 and is related to $L_2$ as follows:

$$\tan \theta_2 = Z_2/L_2$$

$$Z_2 = L_2 \tan \theta_2$$

The average of $Z_1$ and $Z_2$ are calculated and used as the value for Z of the ball. This method is more repeatable and accurate than methods that use only one perspective view per ball.

In still another embodiment of the invention, the method and apparatus disclosed herein is a method and apparatus for calibrating the system by placing a pattern of calibration dots of known spacing and dimensions on the bottom plane of a calibration reticle and for providing a single side perspective view for the three dimensional inspection of parts. From the precision dots the missing state values of the system are determined allowing for three dimensional inspection of balls on BGA devices or balls on wafers or balls on die.

Figure 11A:
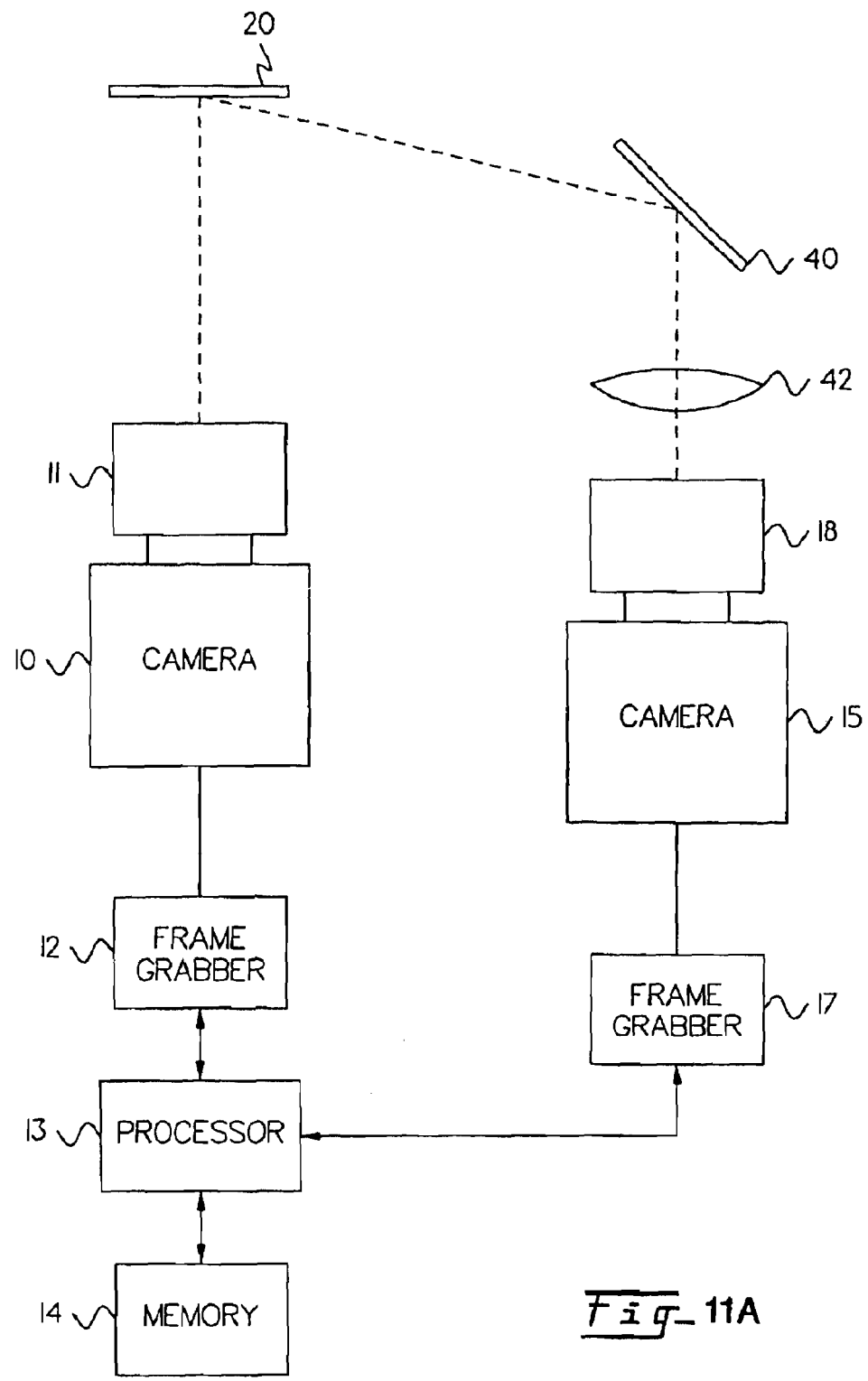
FIG. 11A shows the apparatus of the invention for system calibration, utilizing a single side perspective view.

FIG. 11A shows the apparatus of the invention for system calibration, utilizing a single side perspective view. The method and apparatus for calibration of the bottom view is identical to the method and apparatus described earlier in FIGS. 2A and 2B for the two side perspective views method. The apparatus for an image of a side perspective view includes a camera 15 with a lens 18 and a calibration reticle 20. The camera 15 is located to receive an image 64 of a side perspective view comprising dots 65, described in conjunction with FIG. 11B, and utilizing fixed optical elements 40 and 42. The fixed optical element 40 may be a mirror or prism. The fixed optical element 42 is a nonlinear element that magnifies the image in one direction. In another embodiment fixed optical element 40 may be this nonlinear element. As will be appreciated by those skilled in the art additional optical elements may be incorporated. The camera 15 is connected to a frame grabber board 17 to receive the image 64. The frame grabber board 17 provides an image data output to a processor 13 to perform a two dimensional inspection as described in conjunction with FIG. 2B. The processor 13 may store an image in memory 14.

Figure 11B:
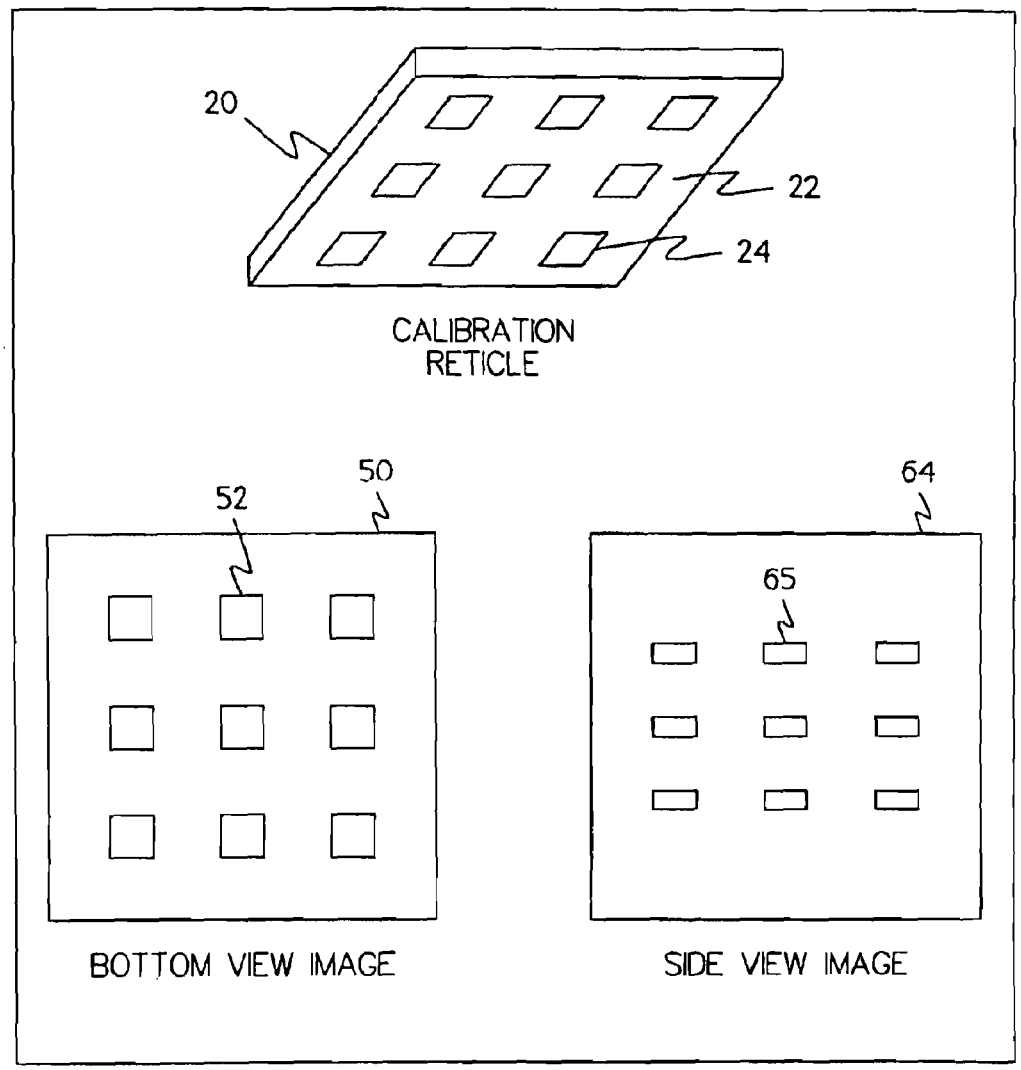
FIG. 11B shows show an example calibration pattern and example images of a calibration pattern acquired by the system, utilizing a single side perspective view, of the invention.

FIG. 11B show an example calibration pattern and example images of a calibration pattern acquired by the system, utilizing a single side perspective view, of the invention. FIG. 11B show an example image 50 from camera 10 and an example image 64 from camera 15 acquired by the system. The image 50 showing dots 52 acquired by camera 10 includes a bottom view of the dot pattern 22, containing precision dots 24 of known dimensions and spacing, located on the bottom surface of the calibration reticle 20. The image 64 shows a side perspective view of the dot pattern 22, containing precision dots 24 of known dimensions and spacing, located on the bottom surface of the calibration reticle 20. A side perspective view in image 64 contains images of dots 65 and is obtained by the reflection of the image of the calibration reticle dot pattern 22 off of fixed optical element 40, passing through nonlinear element 42 and into camera 15.

The side perspective calibration is identical to the method shown in FIG. 2C except the fixed optical elements may have different properties.

The determination of the state values for the side perspective view is identical to the method shown in FIG. 2D except the fixed optical elements may be different and there is only one side perspective view. The principles and relationships shown in FIG. 2E and FIG. 2F apply.

In still another embodiment employing a single side perspective view, the invention does not include the nonlinear element 42.

Figure 12A:
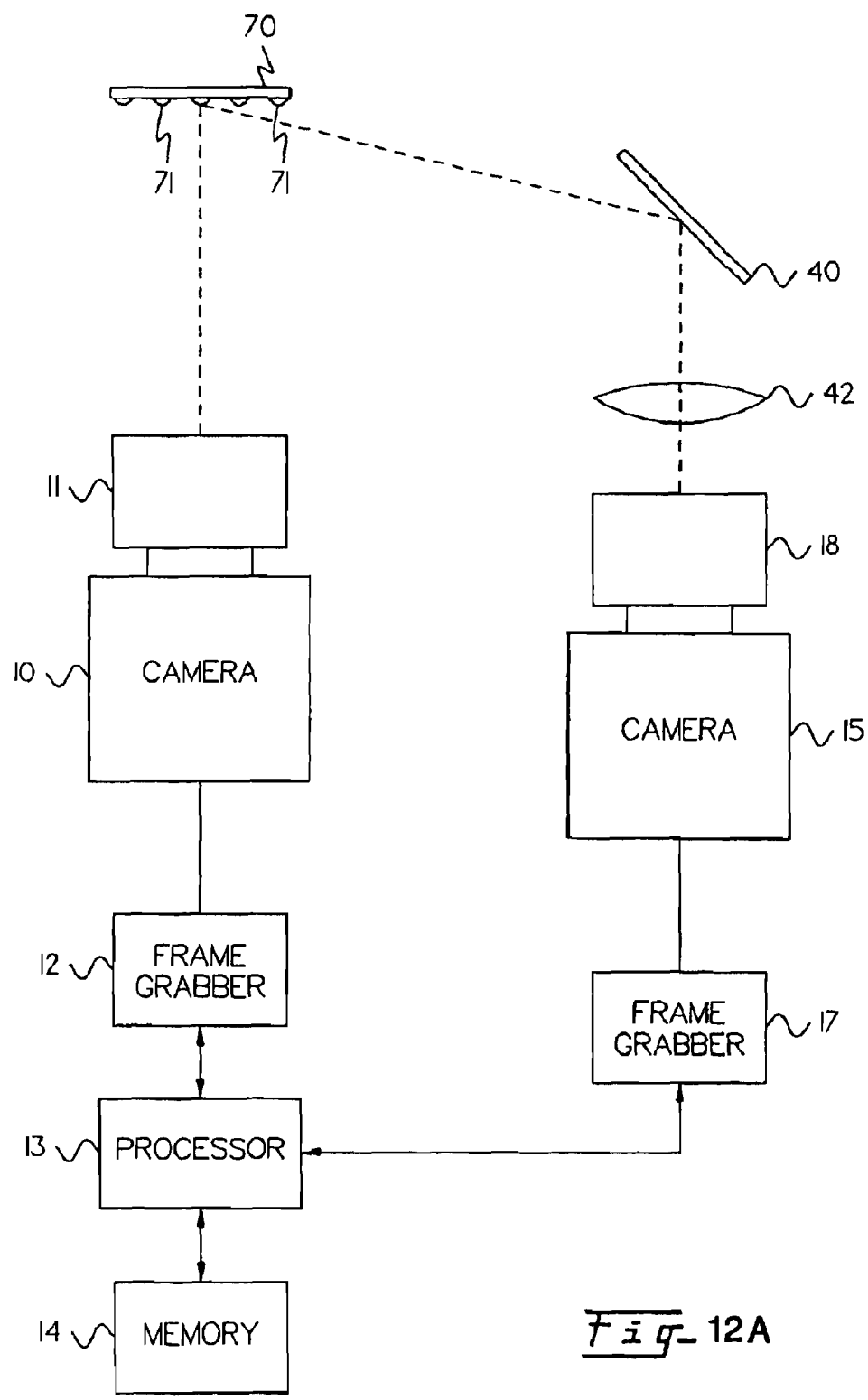
FIG. 12A shows the apparatus of the invention for ball inspection utilizing a single side perspective view.

FIG. 12A shows the apparatus of the invention for ball inspection utilizing a single side perspective view. The apparatus of the invention includes a part 70 to be inspected. The apparatus further includes a camera 10 with a lens 11, located below the central area of part 70, to receive a bottom image 80, described in conjunction with FIG. 12B, of part 70. The camera 10 is connected to a frame grabber board 12 to receive the image 80. The frame grabber board 12 provides an image data output to a processor 13 to perform a two dimensional inspection as described in conjunction with FIG. 12B. The processor 13 may store an image in memory 14. The apparatus for an image of a single side perspective view includes a camera 15 with a lens 18. The camera 15 is located to receive an image 94, comprising a single side perspective view, described in conjunction with FIG. 12B and utilizing fixed optical element 40 and nonlinear, fixed optical element 42, to magnify the side perspective view in one dimension. In another embodiment of the invention optical element 40 may be the nonlinear element. The fixed optical element 40 may be a mirror or prism. As will be appreciated by those skilled in the art additional optical elements may be incorporated. The camera 15 is connected to a frame grabber board 17 to receive the image 94. The frame grabber board 17 provides an image data output to a processor 13 to calculate the Z position of the balls, described in conjunction with FIG. 12B. The processor 13 may store an image in memory 14.

Figure 12B:
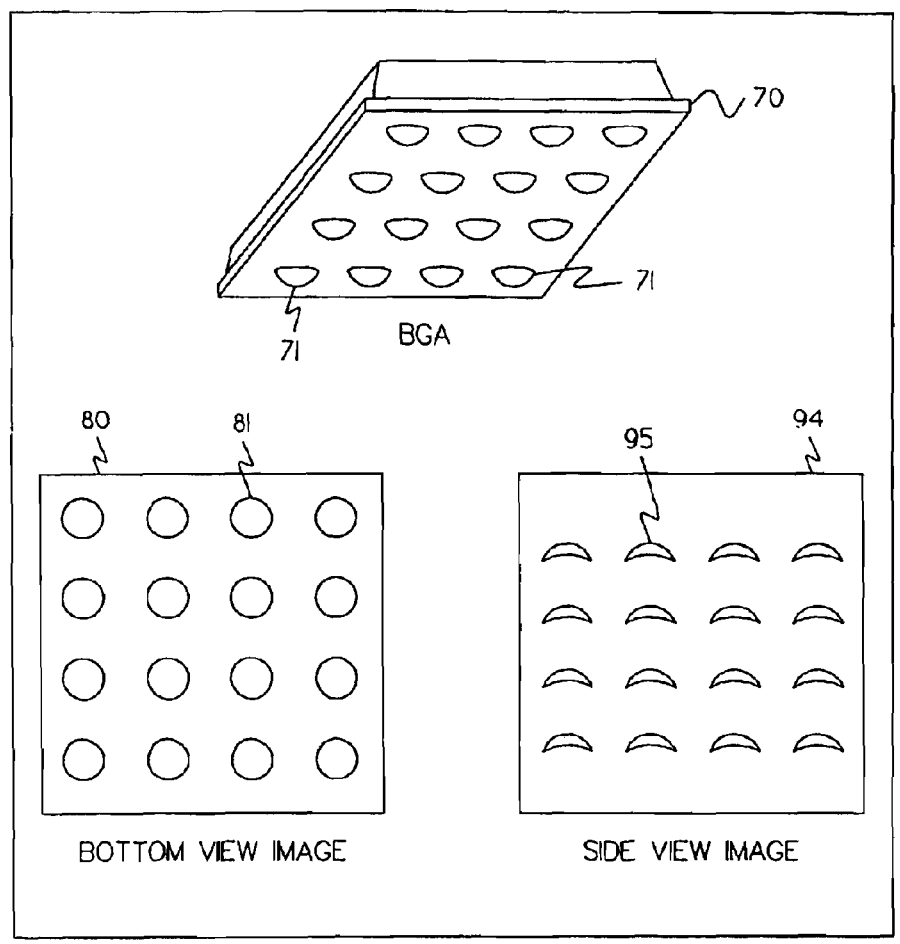
FIG. 12B shows an example ball grid array and example images of the ball grid array for three dimensional inspection, utilizing a single side perspective view.

FIG. 12B shows an example ball grid array and example images of the ball grid array for three dimensional inspection, utilizing a single side perspective view. FIG. 12B shows an example image 80 from camera 10 and an example image 94 from camera 15 acquired by the system. The image 80 shows the bottom view of the balls 71 located on the bottom surface of a part 70. The image 94 shows a side perspective view of the balls 71 located on part 70. The side perspective view in image 94 contains images of balls 95 and is obtained by the reflection of the image of the part 70 off of fixed optical element 40 and passing through the nonlinear fixed element 42 into camera 15.

In an alternate embodiment of the invention, the system can be used to inspect other types of electronic parts in three dimensions, such as (gullwing and J lead devices. By utilizing only one camera and adding an additional set of prisms on the reticle 400 these other devices may be inspected. The advantage of being able to inspect different devices with the same system includes savings in cost, and floor space in the factory. Additionally this design allows more flexibility in production planning and resource management.

FIG. 13 shows the apparatus of the invention for the three dimensional inspection of ball grid array devices, gullwing devices and J lead devices. The apparatus described in FIG. 13 allows the inspection of BGA, gullwing and J lead devices all on the same system. The apparatus includes a part 402 to be inspected located over the central area of a transparent reticle 400 with prisms 401 glued to the top surface to receive side perspective views of part 402. A gullwing and J lead inspection device 21 may be integrated into the ball grid array inspection device. One example embodiment of such a gullwing and J lead inspection device is the "UltraVim" scanner from Scanner Technologies of Minnetonka, Minn. The apparatus further includes a camera 10A with a lens 11A, located below the central area of part 402 and reticle 400 to receive a bottom view and side perspective views of part 402. The camera 10A is connected to a frame grabber board 12A to receive an image. The frame grabber board 12A provides an image data output to a processor 13A to perform a three dimensional inspection of part 402. The processor 13A may store an image in memory 14A. These components comprise the hardware of the gullwing and J lead inspection device 21 and are shared by the ball grid array inspection device as described herein.

The UltraVim is described in U.S. patent application Ser. No. 08/850,473 entitled THREE DIMENSIONAL INSPECTION SYSTEM by Beaty et al., filed May 5, 1997 which is incorporated in its entirely by reference thereto.

Refer now to FIG. 14. In still another embodiment of the invention, the system may use three cameras to image directly the bottom view and two side perspective views as shown in FIG. 14. FIG. 14 shows the apparatus of the invention for a three dimensional inspection of the balls of a BGA. The apparatus of the invention includes a part 70, with balls 71 to be inspected. The apparatus further includes a camera 10 with a lens 11, located below the central area of part 70, to receive a bottom image 80, described in conjunction with FIG. 12B, of part 70. The camera 10 is connected to a frame grabber board 12 to receive the image 80. The frame grabber board 12 provides an image data output to a processor 13 to perform a two dimensional inspection as described in conjunction with FIG. 12B. The processor 13 may store an image in memory 14. The apparatus for an image of a first side perspective view includes a camera 15 with a lens 19. The camera 15 is located to receive an image 94, comprising a single side perspective view, described in conjunction with FIG. 12B and utilizing fixed optical element 38, to magnify the side perspective view in one dimension. The camera 15 is connected to a frame grabber board 17 to receive the image 94. The frame grabber board 17 provides an image data output to a processor 13 to calculate the Z position of the balls, described in conjunction with FIG. 12B. The processor 13 may store an image in memory 14. The apparatus for an image of a second side perspective view includes a camera 15 with a lens 19. The camera 15 is located to receive an image similar to 94, comprising a single side perspective view, described in conjunction with FIG. 12B and utilizing fixed optical element 38, to magnify the side perspective view in one dimension. The camera 15 is connected to a frame grabber board 17 to receive the image similar to 94. The frame grabber board 17 provides an image data output to a processor 13 to calculate the Z position of the balls, described in conjunction with FIG. 12B. The processor 13 may store an image in memory 14. In another embodiment, the nonlinear fixed optical element 38 may be missing. In still another embodiment of the invention, only one side perspective view may be utilized.

In another embodiment of the invention, the method and apparatus disclosed herein is a method and apparatus using a single camera for calibrating the system by placing a pattern of calibration dots of known spacing and size on the bottom plane of a calibration reticle. From the precision dots the missing state values of the system are determined allowing for three dimensional inspection of balls on ball grid array devices, BGA devices or balls on wafers or balls on die.

Figure 15:
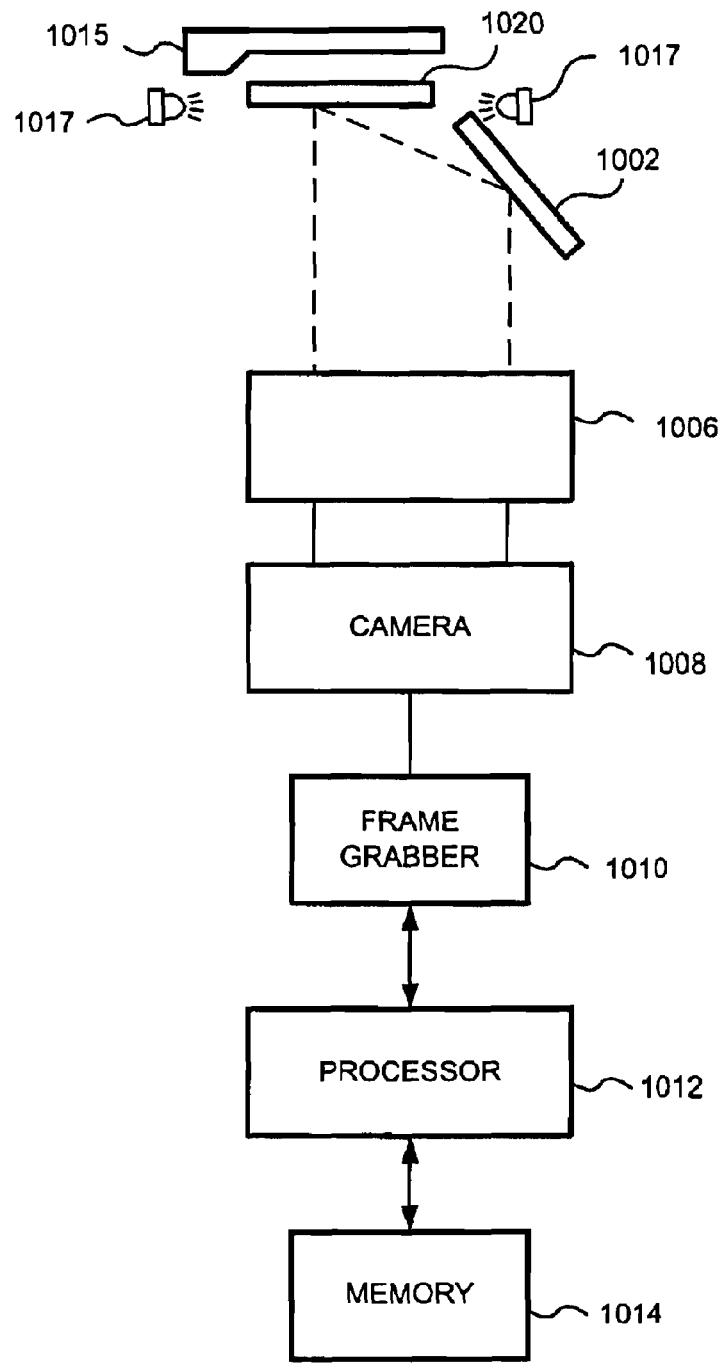
FIG. 15 shows the apparatus of the invention configured with a calibration reticle 1020 for use during calibration of the state values of the system.

Refer now to FIG. 15 which shows one example of the apparatus of the invention configured with a calibration reticle 1020 for use during calibration of the state values of the system. Calibration reticle 1020 is positioned to be viewed by camera 1008. Camera 1008 further comprises a lens 1006. Camera 1008 receives a composite image of the calibration reticle 1020, one portion of the image, through mirror 1002 and an additional portion directly. A frame grabber 1010 receives image information from the camera 1008 and provides processor 1012 with image information of the calibration reticle 1020. The image information and other inspection information may be stored in memory 1014. The apparatus obtains an image 1024 showing a bottom view 1026 containing an image 1031 of a precision dot 1030 and a side view 1028 containing an image 1032 of precision dot 1030 of the calibration reticle 1020 shown in FIG. 16A. This image 1024 is shown in FIG. 16B. To take the image 1024, the apparatus includes a means of illumination 1017, an overhead light diffuser 1015, the camera 1008, with lens 1006, and calibration reticle 1020 with a calibration pattern 1022 on the bottom surface of the calibration reticle 1020. A separate optical element 1002 is positioned below the calibration reticle 1020 to provide an additional perspective or side view 1028 containing an image of precision dot 1032 of the calibration reticle 1020.

In one embodiment of the invention, the optical element 1002 may comprise a prism. In another embodiment of the invention, the optical element 1002 may comprise a mirror. As will be appreciated by one skilled in the art, the invention will work with any number of side views. The calibration pattern 1021 on the reticle 1020 comprises precision dots 1022. The camera 1008 is located below the central part of the calibration reticle 1020 to receive an image 1024 described in conjunction with FIGS. 16A and 16B. In one embodiment of the invention, the camera 1008 comprises an image sensor. The image sensor may be a charged coupled device array. The camera 1008 is connected to a frame grabber board 1010 to receive the image 1024. The frame grabber board 1010 provides an image data output to a processor 1012 to perform a three dimensional calibration as described in conjunction with FIG. 16B. The principles and relationships shown in FIGS. 2E and 2F apply. The processor 1012 may store an image in memory 1014.

Figure 16A:
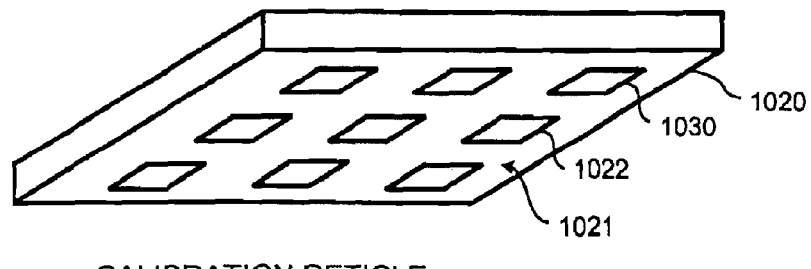
FIGS. 16A and 16B show an example calibration pattern and example images of the calibration pattern acquired by the single camera system.
Figure 16B:
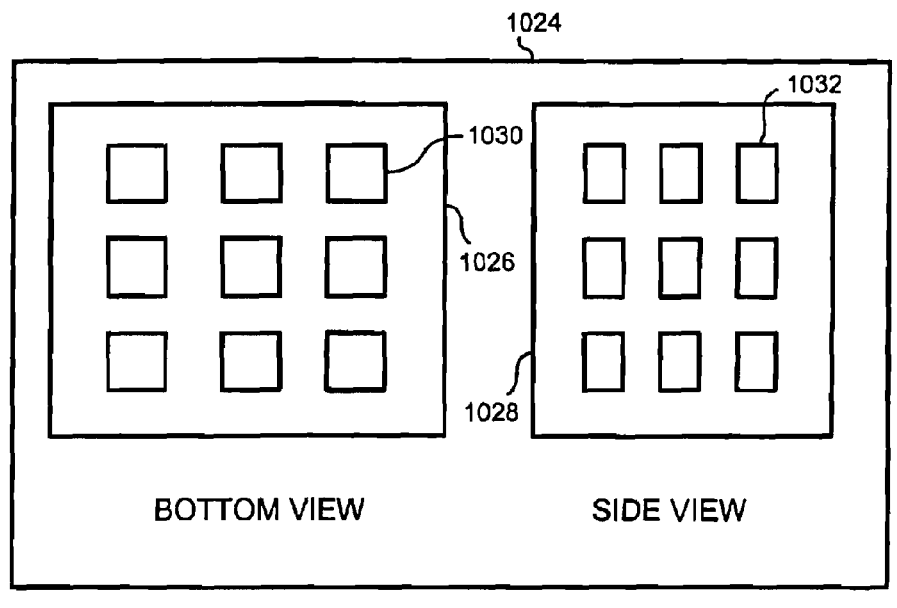

Now refer to FIGS. 16A and 16B which show a calibration reticle 1020 having precision dots 1022. FIG. 16B shows a composite image 1024 of the calibration reticle 1020. The bottom view 1026 shows precision dot 1030 with a first perspective view 1031 and a side view 1028 shows precision dot 1030 with a second perspective view 1032. The system processor processes the composite image 1024 according to the system of equations described herein with the bottom view 1026 and side view 1028 providing information for the solution of the system of equations. The principles and relationships shown in FIG. 2E and FIG. 2F apply.

In another embodiment of the invention, the method and apparatus disclosed herein is a method and apparatus using a single camera for a three dimensional inspection of balls on ball grid array devices, BGA/CSP devices or balls on wafers or balls on die.

Figure 17:
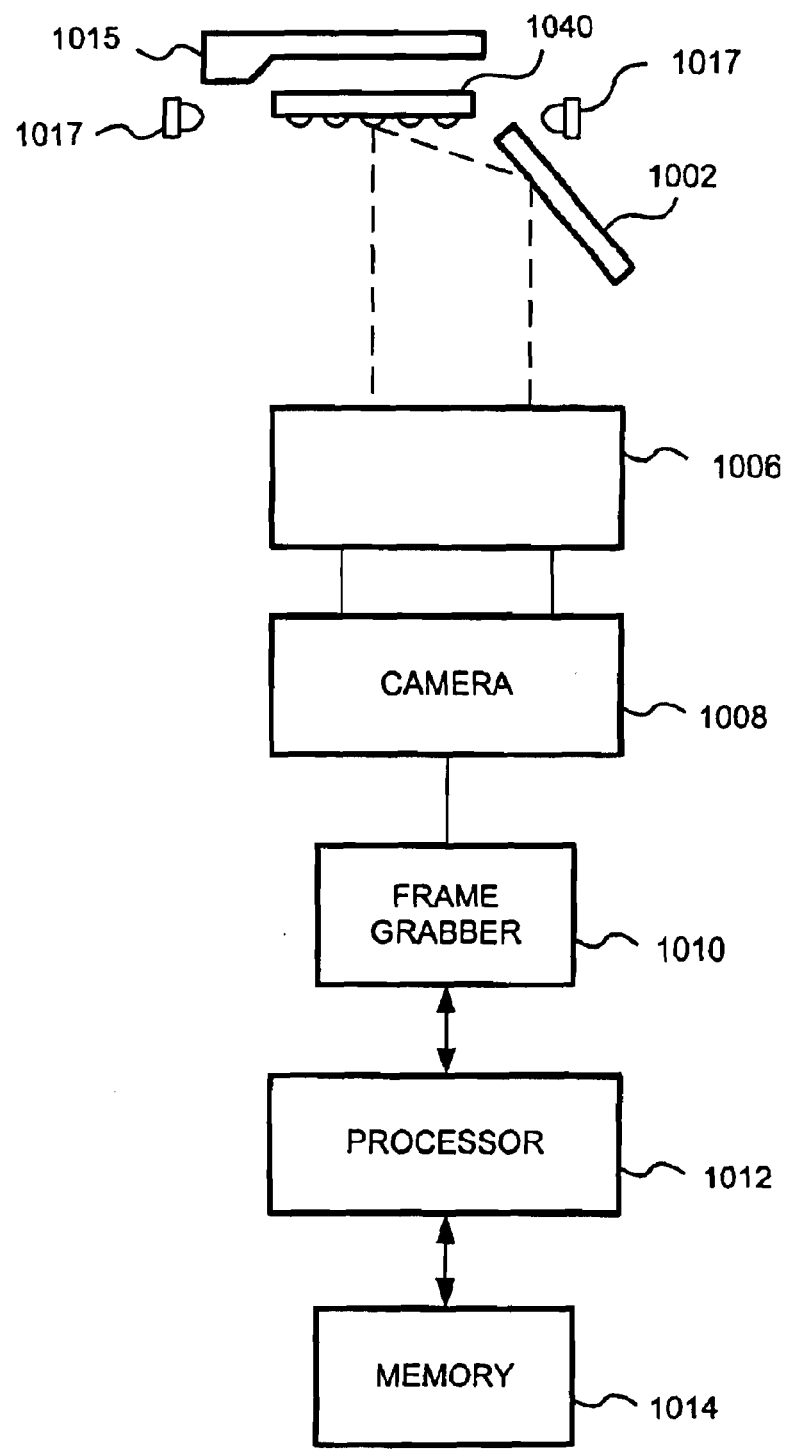
FIG. 17 shows the apparatus of the invention configured with a part 1040 to be inspected by the system.

Refer now to FIG. 17 which shows the apparatus of the invention configured with a part 1040 to be inspected by the system. The apparatus obtains an image 1044 showing a bottom view 1046 containing an image of a ball 1050 and a side view 1048 containing an image of a ball 1052 of the part 1040. To take the image 1044, the apparatus includes a means of illumination 1017 which may be a ring light, camera 1008 with a first optical element, lens 1006, and a part 1040 with a ball 1042 on the bottom surface. In one embodiment of the invention, the means of illumination 1017 lights the bottom surface of the part 1040 to allow imaging the perimeter of the part 1040. In another embodiment of the invention, overhead diffuser 1015 provides illumination for imaging of the perimeter of the part 1040.

In one example, the means for illumination may comprise reflected light, the lens 1006 may comprise a plurality of lens elements, a pin hole lens or a telecentric lens, and the processor 1012 may comprise a personal computer. Those skilled in the art will understand that the output of the sensor may be transmitted directly to memory without the use of a frame grabber.

A separate second optical element 1002 is positioned below the bottom plane of part 1040 to provide an additional perspective or side view 1048 of the part 1040 containing an image of the ball 1052 of the part 1040. In one embodiment of the invention, the optical element 1002 may comprise a prism. In another embodiment of the invention, the optical element 1002 may comprise a mirror. As will be appreciated by one skilled in the art, the invention will work with any number of side views. The camera 1008 is located below the central part of the part 1040 to receive an image 1044 described in conjunction with FIGS. 18A and 18B. In one embodiment of the invention, the camera 1008 comprises an image sensor. The image sensor may be a charged coupled device array or a complementary metal oxide semiconductor device array. The camera 1008 is connected to a frame grabber board 1010 to receive the image 1044. The frame grabber board 1010 provides an image data output to a processor 1012 to perform a three dimensional inspection of the part 1040 as described in conjunction with FIGS. 18A and 18B. The principles and relationships shown in FIG. 6A and FIG. 6B apply. The processor 1012 may store an image in memory 1014.

Figure 18A:
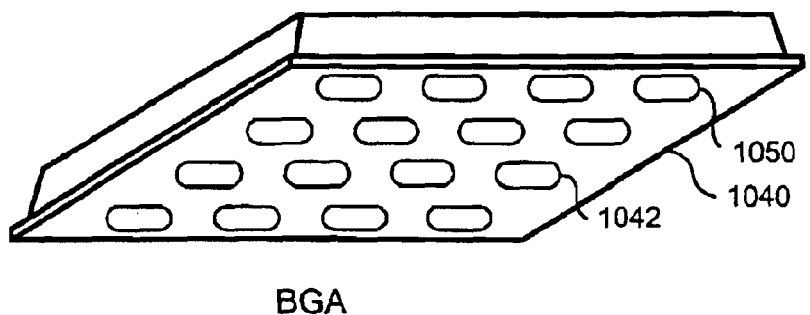
FIGS. 18A and 18B show a part and example images of a part acquired by the system.
Figure 18B:
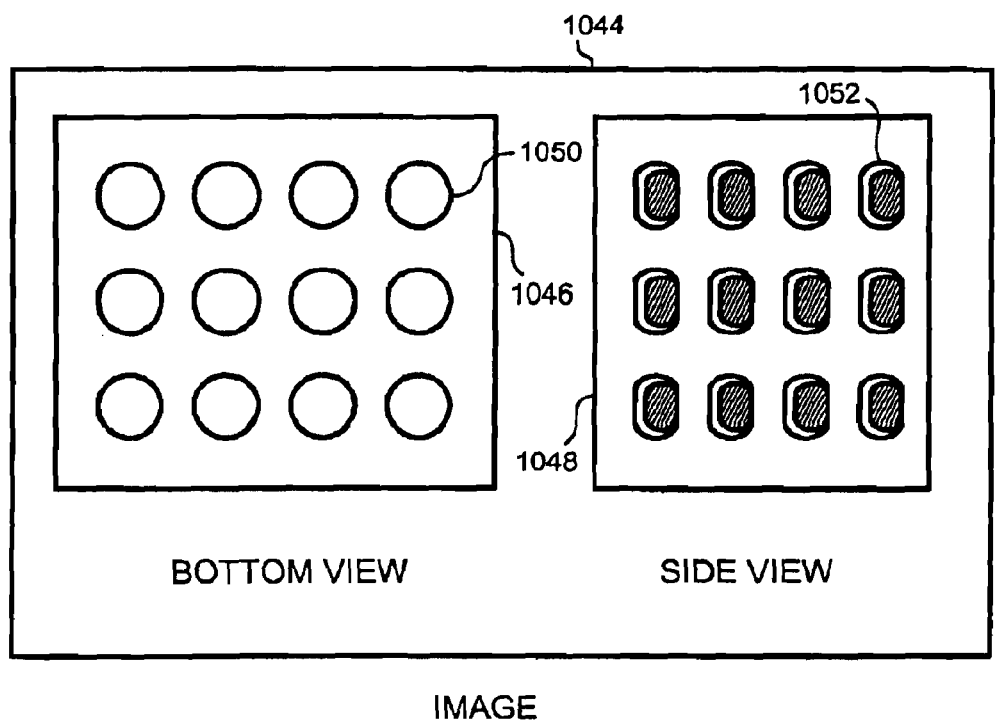

Now refer to FIGS. 18A and 18B which shows a ball grid array 1040 having balls 1042. FIG. 18B shows a composite image 1044 of the ball grid array 1040. The bottom view 1046 shows ball 1050 with a first perspective view 1051 and a side view 1048 shows ball 1050 with crescent shape 1052 with a second perspective view. The system processor processes the composite image 1044 according to the system of equations described herein with the bottom view 1046 and side view 1048 providing information for the solution of the system of equations. The principles and relationships shown in FIG. 6A and FIG. 6B apply.

A method of manufacturing ball array devices using an inspection apparatus having one or more cameras and ball array devices produced according to the method have been described. It will be understood by those skilled in the art that the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. A method of manufacturing a ball array device having a plurality of leads, the method comprising:
   providing a fixed optical imaging system comprising at least one camera;
   calibrating the fixed optical imaging system with a planar precision pattern disposed in a fixed position;
   obtaining a single bottom view image of the leads using the calibrated system;

obtaining a single side view image of the leads using the calibrated system;

calculating an inspection result by combining information from the single bottom view image and the single side view image; and selecting the ball array device as a manufactured product using the calculated inspection result.

2. The method of claim 1, wherein the ball array device is selected from the group consisting of: ball grid array, ball grid array socket, bump on wafer, ceramic ball grid array, chip array ball grid array, chip scale product, flip chip ball grid array, flip chip scale product, high performance ball grid array, land grid array, land grid array socket, leadless chip carrier, micro lead frame, plastic ball grid array, super ball grid array, super flip chip, system in a package, and thin chip array ball grid array.

3. The method of claim 1, wherein the plurality of leads is selected from the group consisting of: bumps, balls, columns, contacts, pads, pins, towers, posts, micro-pins, and pedestals.

4. The method of claim 1, wherein the fixed optical imaging system comprises at least one camera, at least one lens, at least one illumination source, at least one processor and memory.

5. The method of claim 1, wherein the fixed optical imaging system comprises a camera, optics, illumination and a computer.

6. The method of claim 1, wherein the planar precision pattern is selected from the group consisting of: calibration reticle, precision pattern that is generally planar, precision pattern of fiducials disposed on a generally planar surface, precision pattern on a metal surface and precision pattern on a glass surface.

7. The method of claim 1, wherein the information from the single bottom view image and the single side view image is selected from the group consisting of: a subpixel position of the center of a donut shaped reflection, a subpixel position of the center of a crescent shaped reflection, a subpixel position of the top of a crescent shaped reflection, a subpixel position of the center of an ellipse shaped reflection, a subpixel position of the top of an ellipse shaped reflection, a Db displacement in the single bottom view image, a Ds displacement in the single side view image, a world location, and a subpixel location relative to the stored locations of at least three calibration fiducials.

8. The method of claim 1, wherein the inspection result is selected from the group consisting of: pass, rework, invalid, not found, reject and fail.

9. The method of claim 1, wherein the manufactured product is selected from the group consisting of: finished good, assembled ball array device, finished ball array device, accepted ball array device, ball array device ready for packaging, ball array device ready for shipping, and ball array device ready to be passed on to a subsequent manufacturing step.

10. The method of claim 1, wherein calculating an inspection result comprises calculating a Z value for each of the leads.

11. The method of claim 1, wherein calculating an inspection result comprises calculating a coplanarity value for each of the leads.

12. The method of claim 1, wherein calculating an inspection result comprises calculating a coplanarity value for each lead, calculating a maximum coplanarity value, and comparing the maximum coplanarity value to a predetermined tolerance value.

13. The method of claim 1, wherein selecting the ball array device comprises providing a result signal to a part handler based upon the inspection result.

14. The method of claim 1, wherein selecting the ball array device comprises selecting the ball array device as an acceptable device to be passed to a subsequent manufacturing step based upon the inspection result.

15. An electronic product comprising the ball array device manufactured by the method of claim 1 wherein the electronic product is selected from the group consisting of: automotive controller, personal computer, digital camera, graphics board, memory device, motherboard, music player, networking device, telephone, cell phone, television, video game console and video player.

16. A method of manufacturing a ball array device having a plurality of leads, the method comprising:

providing a fixed optical imaging system comprising at least one camera;

calibrating the fixed optical imaging system with a planar precision pattern disposed in a fixed focus position;

obtaining a bottom view image comprising donut shaped reflections from the leads using the calibrated system;

obtaining a side view image comprising crescent shaped reflections from the leads using the calibrated system;

finding locations of the donut shaped reflections from the leads;

finding locations of the crescent shaped reflections from the leads;

calculating a Z value for each lead by combining information from the locations of the donut shaped reflections and the locations of the crescent shaped reflections;

calculating a coplanarity value for the ball array device by using the Z value for each lead; and determining an inspection result by comparing the coplanarity value to a predetermined tolerance value; and selecting the ball array device based upon the inspection result.

17. A method of manufacturing a ball array device having a plurality of leads, the method comprising:

providing an imaging system with at least one camera, at least one lens, at least one illumination source, at least one processor and memory;

obtaining a single bottom view image of the leads using the imaging system;

obtaining a single side view image of the leads using the imaging system;

finding a subpixel location of each lead in the single bottom view image;

finding a subpixel location of each lead in the single side view image;

calculating a Z value for each lead by combining information from the subpixel location of the lead in the single bottom view image and the subpixel location of the same lead in the single side view image;

calculating a coplanarity value for the ball array device by using information from the Z value of each lead and parameters determined during a calibration;

determining an inspection result by comparing the coplanarity value to a predetermined tolerance value; and selecting the ball array device based upon the inspection result.

18. A method of manufacturing a ball array device having a plurality of leads, the method comprising:

providing a fixed optical imaging system comprising at least one camera, at least one lens, at least one illumination source, at least one processor and memory;

calibrating the imaging system with a planar precision pattern disposed in a fixed focus position;

obtaining a single bottom view image of the leads using the calibrated imaging system;

obtaining a single side view image of the leads using the calibrated imaging system;

finding a subpixel location of a reflection from each lead in the single bottom view image;

finding a subpixel location of a reflection from each lead in the single side view image;

calculating a Z value for each lead by combining information from the subpixel location of a reflection from the lead in the single bottom view image and the subpixel location of the reflection from the same lead in the single side view image;

calculating a coplanarity value for the ball array device by using information from the Z value of each lead;

determining an inspection result by comparing the coplanarity value to a predetermined tolerance value; and selecting the ball array device based upon the inspection result.

19. A method of manufacturing a ball array device having a plurality of leads, the method comprising:

providing an imaging system comprising at least one camera;

calibrating the imaging system with a planar precision pattern disposed in a fixed focus position;

obtaining two differing views of the leads in at least one image using the calibrated imaging system;

obtaining a donut shaped reflection from each lead and a crescent shaped reflection from each lead in the at least one image;

finding at least two reference positions of each lead in the at least one image;

calculating a Z value of each lead using the at least two reference positions of each lead;

calculating a coplanarity value using information from the Z value of each lead;

determining an inspection result by comparing the coplanarity value to a tolerance value; and selecting the ball array device as a manufactured product depending upon the inspection result.

20. A ball array device having a plurality of leads, the device being produced according to a process comprising:

providing a fixed optical imaging system comprising at least one camera;

calibrating the fixed optical imaging system with a planar precision pattern disposed in a fixed position;

obtaining a single bottom view image of the leads using the calibrated system;

obtaining a single side view image of the leads using the calibrated system;

calculating an inspection result by combining information from the single bottom view image and the single side view image; and selecting the ball array device as a manufactured product using the calculated inspection result.

21. The ball array device of claim 20, wherein the ball array device is selected from the group consisting of: ball grid array, ball grid array socket, bump on wafer, ceramic ball grid array, chip array ball grid array, chip scale product, flip chip ball grid array, flip chip scale product, high performance ball grid array, land grid array, land grid array socket, leadless chip carrier, micro lead frame, plastic ball grid array, super ball grid array, super flip chip, system in a package, and thin chip array ball grid array.

22. The ball array device of claim 20, wherein the plurality of leads is selected from the group consisting of: bumps, balls, columns, contacts, pads, pins, towers, posts, micro-pins, and pedestals.

23. The ball array device of claim 20, wherein the fixed optical imaging system comprises at least one camera, at least one lens, at least one illumination source, at least one processor and memory.

24. The ball array device of claim 20, wherein the fixed optical imaging system comprises a camera, optics, illumination and a computer.

25. The ball array device of claim 20, wherein the planar precision pattern is selected from the group consisting of: calibration reticle, precision pattern that is generally planar, precision pattern of fiducials disposed on a generally planar surface, precision pattern on a metal surface and precision pattern on a glass surface.

26. The ball array device of claim 20, wherein the information from the single bottom view image and the single side view image is selected from the group consisting of: a subpixel position of the center of a donut shaped reflection, a subpixel position of the center of a crescent shaped reflection, a subpixel position of the top of a crescent shaped reflection, a subpixel position of the center of an ellipse shaped reflection, a subpixel position of the top of an ellipse shaped reflection, a Db displacement in the single bottom view image, a Ds displacement in the single side view image, a world location, and a subpixel location relative to the stored locations of at least three calibration fiducials.

27. The ball array device of claim 20, wherein the inspection result is selected from the group consisting of: pass, rework, invalid, not found, reject and fail.

28. The ball array device of claim 20, wherein the ball array device selected as a manufactured product is selected from the group consisting of: finished good, assembled ball array device, finished ball array device, accepted ball array device, ball array device ready for packaging, ball array device ready for shipping, and ball array device ready to be passed on to a subsequent manufacturing step.

29. The ball array device of claim 20, wherein calculating an inspection result comprises calculating a Z value for each of the leads.

30. The ball array device of claim 20, wherein calculating an inspection result comprises calculating a coplanarity value for each of the leads.

31. The ball array device of claim 20, wherein calculating an inspection result comprises calculating a coplanarity value for each lead, calculating a maximum coplanarity value, and comparing the maximum coplanarity value to a predetermined tolerance value.

32. An electronic product comprising the ball array device of claim 20, wherein the electronic product is selected from the group consisting of: automotive controller, personal computer, digital camera, graphics board, memory device, motherboard, music player, networking device, telephone, cell phone, television, video game console and video player.

33. A ball array device having a plurality of leads, the device being produced according to a process comprising:

providing a fixed optical imaging system comprising at least one camera;

calibrating the fixed optical imaging system with a planar precision pattern disposed in a fixed focus position;

obtaining a bottom view image comprising donut shaped reflections from the leads using the calibrated system;

obtaining a side view image comprising crescent shaped reflections from the leads using the calibrated system;

finding locations of the donut shaped reflections from the leads;

finding locations of the crescent shaped reflections from the leads;

calculating a Z value for each lead by combining information from the locations of the donut shaped reflections and the locations of the crescent shaped reflections;

calculating a coplanarity value for the ball array device by using the Z value for each lead; and determining an inspection result by comparing the coplanarity value to a predetermined tolerance value; and selecting the ball array device based upon the inspection result.

34. A ball array device having a plurality of leads, the device being produced according to a process comprising:

providing an imaging system with at least one camera, at least one lens, at least one illumination source, at least one processor and memory;

obtaining a single bottom view image of the leads using the imaging system;

obtaining a single side view image of the leads using the imaging system;

finding a subpixel location of each lead in the single bottom view image;

finding a subpixel location of each lead in the single side view image;

calculating a Z value for each lead by combining information from the subpixel location of the lead in the single bottom view image and the subpixel location of the same lead in the single side view image;

calculating a coplanarity value for the ball array device by using information from the Z value of each lead and parameters determined during a calibration;

determining an inspection result by comparing the coplanarity value to a predetermined tolerance value; and selecting the ball array device based upon the inspection result.

35. A ball array device having a plurality of leads, the device being produced according to a process comprising:

providing a fixed optical imaging system comprising at least one camera, at least one lens, at least one illumination source, at least one processor and memory;

calibrating the imaging system with a planar precision pattern disposed in a fixed focus position;

obtaining a single bottom view image of the leads using the calibrated imaging system;

obtaining a single side view image of the leads using the calibrated imaging system;

finding a subpixel location of a reflection from each lead in the single bottom view image;

finding a subpixel location of a reflection from each lead in the single side view image;

calculating a Z value for each lead by combining information from the subpixel location of a reflection from the lead in the single bottom view image and the subpixel location of the reflection from the same lead in the single side view image;

calculating a coplanarity value for the ball array device by using information from the Z value of each lead;

determining an inspection result by comparing the coplanarity value to a predetermined tolerance value; and selecting the ball array device based upon the inspection result.

36. A ball array device having a plurality of leads, the device being produced according to a process comprising:

providing an imaging system comprising at least one camera;

calibrating the imaging system with a planar precision pattern disposed in a fixed focus position;

obtaining two differing views of the leads in at least one image using the calibrated imaging system;

obtaining a donut shaped reflection from each lead and a crescent shaped reflection from each lead in the at least one image;

finding at least two reference positions of each lead in the at least one image;

calculating a Z value of each lead using the at least two reference positions of each lead;

calculating a coplanarity value using information from the Z value of each lead;

determining an inspection result by comparing the coplanarity value to a tolerance value; and selecting the ball array device as a manufactured product depending upon the inspection result.

* * * * *